(12) United States Patent
Fogh et al.

(10) Patent No.: US 7,148,048 B2
(45) Date of Patent: Dec. 12, 2006

(54) PROCESS FOR PURIFICATION OF RECOMBINANT PORPHOBILINOGEN DEAMINASE

(75) Inventors: Jens Fogh, Hillerod (DK); Claes Andersson, Taby (SE)

(73) Assignee: Zymenex A/S, Hillerod (DE)

( * ) Notice: Subject to any disclaimer, the term of this patent is extended or adjusted under 35 U.S.C. 154(b) by 0 days.

(21) Appl. No.: 10/318,360

(22) Filed: Dec. 13, 2002

(65) Prior Publication Data

US 2003/0180926 A1  Sep. 25, 2003

Related U.S. Application Data

(63) Continuation-in-part of application No. PCT/DK02/00452, filed on Jun. 28, 2002.

(30) Foreign Application Priority Data

Jun. 29, 2001 (DK) ............................... 2001 01018

(51) Int. Cl.
- C12N 9/10 (2006.01)
- A23J 1/00 (2006.01)
- C12N 1/21 (2006.01)
- C07H 21/04 (2006.01)

(52) U.S. Cl. .............. 435/193; 435/252.3; 435/252.33; 435/325; 530/412; 530/413; 530/416; 536/23.2

(58) Field of Classification Search ................ 435/232, 435/252.3, 252.33, 814, 815, 193, 320.1, 435/325; 530/412, 413; 536/23.2
See application file for complete search history.

(56) References Cited

U.S. PATENT DOCUMENTS 6,537,777 B1 * 3/2003 Gellerfors et al. ......... 435/69.1

FOREIGN PATENT DOCUMENTS

WO  0107065  2/2001

OTHER PUBLICATIONS

Amersham Pharmacia Biotech Catalog, 1999, p. 553.*
Knight et al. (1981) J. Biol. Chem., vol. 256, No. 8, pp. 3609-3611.*
Smythe et al., *A simple rapid purification scheme for hydroxymethylbilane synthase from human erythrocytes*, Biochem. J., vol. 251, pp. 237-241, 1988.

Waldenström et al., "Studien über Porphyrie", Acta Medica Scandinavica, Suppl. LXXXII, Stockholm, 1937 (Abstract in English).

Baksi et al., *Rapid, Single-Step Purification of Restriction Endonucleases on Cibacron Blue F3GA-Agarose*, American Chemical Society, Biochemistry, vol. 17, No. 20, pp. 4136-4139, 1978.

Kirchberger et al., *Preparation of Homogeneous Alkaline Phosphatase from Calf Intestine by Dye-Ligand Chronatography*, Preparative Biochemistry, vol. 12, No. 1, pp. 29-47, 1982.

Satoshi Inouye, *NAD(P)H-flavin oxidoreductase from the bioluminescent bacterium, Vibrio fischeri ATCC 7744, is a flavoprotein*, FEBS Letters, vol. 347, pp. 163-168, 1994.

Lannfelt et al., *Porphobilinogen deaminase in human erythrocytes: purification of two forms with apparent molecular weights of 40 kDa and 42 kDa*, Scand. J. Clin. Lab. Invest., 1989.

F.W.M. De Rooij et al., *Purification of porphobilinogen deaminase from human erythrocytes by fast protein liquid chromatography*, Clinica Chimica Acta, vol. 162, pp. 61-68, 1987.

Mazzetti et al., *Characterization of porphobilinogen deaminase from rat liver*. Biochimica et Biophysica Acta, vol. 957, pp. 97-104, 1988.

Hart et al., *Purification, N-terminal amino acid sequence and properties of hydroxymethylbilane synthase(porphobilinogen deaminase)from Escherichia coli*, Biochem. J. vol. 240, pp. 273-276, 1986.

Miyagi et al., *Uroporphyrinogen I synthase from human erythrocytes: Separation, purification, and properties of isoenzymes*. Proc. Natl. Acad. Sci., vol. 76, No. 12, pp. 6172-6176, Dec. 1979.

Jordan et al., *IPurification, crystallization and properties of porphobilinogen deaminase from a recombinant strain of Escherichia coli K12*, Biochem. H., vol. 254, pp. 427-435, 1988.

Hadener et al., *Purification, characterization, crystallization and X-ray analysis of selenomethionine-labelled hydroxymethylbilane synthase from Escherichia coli*, Natl. J. Biochem., vol. 211, pp. 615-624, 1993.

Anderson et al., *Purification and properties of Uroporphyrinogen I Synthase from Human Erythrocytes*, J. Biol. Chem., vol. 255, No. 5, pp. 1993-1999, Mar. 10, 1980.

* cited by examiner

Primary Examiner—Elizabeth Slobodyansky
(74) Attorney, Agent, or Firm—Iver P. Cooper

(57) ABSTRACT

A process for purification of recombinant porphobilinogen deaminase (rhPBGD) on an industrial scale by starting from a rhPBGD containing extract obtained from a fermentation of a recombinant cell capable of expressing the rhPBGD and the use of the purified product for the preparation of a medicament.

15 Claims, 7 Drawing Sheets

PROCESS FOR PURIFICATION OF RECOMBINANT PORPHOBILINOGEN DEAMINASE

FIELD OF THE INVENTION

Figure 1:
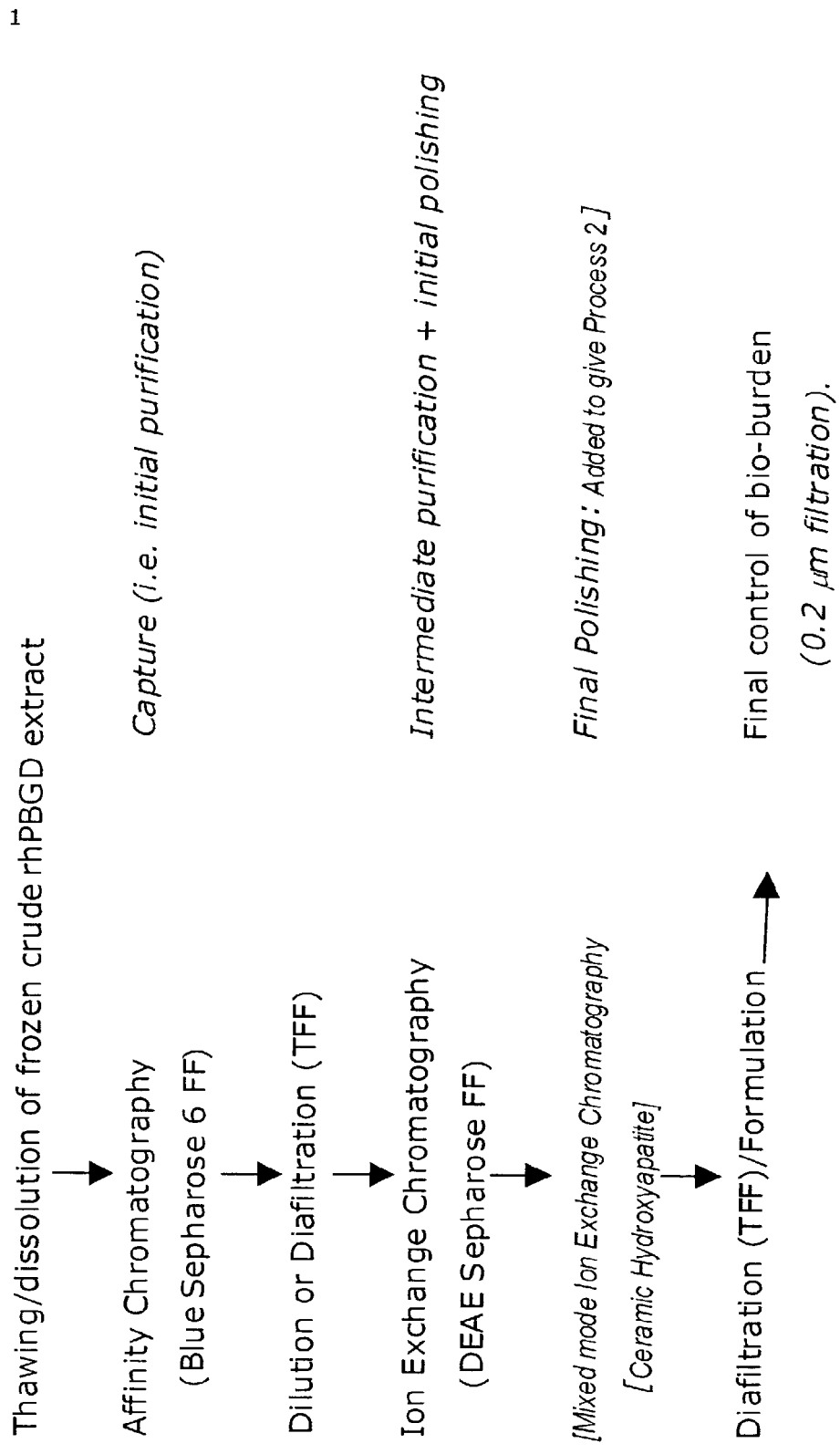

The present invention relates to a process for purification of recombinant porphobilinogen deaminase (rhPBGD) on an industrial scale by starting from a rhPBGD containing extract obtained from a fermentation of a recombinant cell capable of expressing the rhPBGD. It furthermore relates to the use of the purified product for the preparation of a medicament which is effective in lowering the porphobilinogen (PBG) level in patients with acute intermittent porphyria (AIP).

BACKGROUND OF THE INVENTION

Porphobilinogen deaminase, (also known as porphobilinogen ammonia-lyase (polymerizing)), E.C. 4.3.1.8. (Waldenström 1937, J. Acta. Med. Scand. Suppl. 8) is the third enzyme in the heme biosynthetic pathway. In the following, this enzyme and the recombinant human form will be termed "PBGD" and "rhPBGD", respectively.

PBGD is important in relation to Acute intermittent porphyria (AIP), which is an autosomal dominant disorder in man caused by a defect (50% reduction of activity) of PBGD (see WO01/07065 for further details in relation to this).

Smythe et al. (Biochem. J. (1988) 251:237–241) describes a purification protocol for PBGD. The volume of the PBGD containing extract loaded on the specified chromatography columns is less than 1 L (see table 1). In the present context this is considered a small-scale laboratory purification protocol. The described protocol comprises first loading the PBGD containing extract on a Ion-exchange column (DEAE-cellulose) followed by use of an affinity column (Cibacron Blue FG3-A-Sepharose).

In relation to an upscaled purification protocol for rhPBGD, WO01/07065 describes in example 7 a high scale fermentation process using a recombinant E.coli cell capable of expressing the rhPBGD followed by a down-stream purification process. The purification process comprises loading a rhPBGD containing extract, obtained from the fermentation, on Hydrophobic interaction chromatography (HIC) column followed by a Ion-exchange chromatography CIEC) step, ending with an affinity step on Cibacron Blue FF Sepharose. The used column volumes are around 10 to 12 L.

SUMMARY OF THE INVENTION

The problem to be solved by the present invention is to provide an improved process for purification of recombinant porphobilinogen deaminase (rPBGD) on an industrial scale.

The solution is based on the finding by the present inventors that by loading, as the first chromatography step, the (rPBGD) containing extract on an affinity chromatography column it is possible, already after this first chromatography step, to obtain a sample which is relatively pure and very stable due to that the majority of the contaminants have been removed (see example 1 herein for a description).

Accordingly, a first aspect of the invention relates to a process for purification of recombinant porphobilinogen deaminase (rPBGD), especially recombinant human porphobilinogen deaminase (rhPBGD) on an industrial scale by starting from a rhPBGD containing extract obtained from a fermentation of a recombinant cell capable of expressing the rhPBGD and which process is characterized by following steps:

(i): loading the rhPBGD containing extract on an equilibrated affinity chromatography column having a column volume of at least 5 L and, after adequate washing step(s) eluting a sample comprising rhPBGD;

(ii) loading the eluent of step (i) on an equilibrated chromatography column having a column volume of at least 5 L and, after adequate washing step(s), eluting a sample comprising rhPBGD;

(iii) optionally, performing one or more further chromatography column step(s);

(iv): formulating the sample to obtain a sample comprising the rhPBGD in a suitable formulation buffer;

(v): filing the formulated sample into a suitable receiver.

An advantage of using an affinity chromatography column, as the first chromatography column step is that in one step the majority of the contaminants are removed. This gives a stable rhPBGD containing sample which is suitable to work with in further large scale steps. On the contrary, having a Ion-exchange chromatography (IEC) step before the affinity chromatography step results in an IEC eluted sample that still contains contaminating components such as porphyrins (known to be very sticky and difficult to remove), which makes it hard to continue further large scale steps.

A further advantage is that the affinity chromatography step gives, already after this one purification step, a sample which contains rhPBGD in a very pure form.

Definitions

Prior to a discussion of the detailed embodiments of the invention is provided a definition of specific terms related to the main aspects of the invention.

The term "recombinant porphobilinogen deaminase (rhPBGD)" denotes herein a recombinant produced PBGD. Porphobilinogen deaminase, (also known as porphobilinogen ammonia-lyase (polymerizing)), E.C. 4.3.1.8. (Waldenström 1937, J. Acta. Med. Scand. Suppl. 8) is the third enzyme in the heme biosynthetic pathway. In the following, this enzyme and the recombinant human form will be termed "PBGD" and "rhPBGD", respectively. When this term is used, it should be understood that the disclosed methods may also be applied, mutatis mutandis, to production or purification of an enzymatically equivalent part or analogue of rhPBGD. One example of an enzymatically equivalent part of the enzyme could be a domain or subsequence of the enzyme which includes the necessary catalytic site to enable the domain or subsequence to exert substantially the same enzymatic activity as the full-length enzyme or alternatively a gene coding for the catalyst. The term "substantially the same enzymatic activity" refers to an enzyme having at least 50%, preferably at least 75%, more preferably at least 95%, of the activity of natural human rhPBGD measured in the rhPBGD activity assay shown in working example 2 herein. An example of an enzymatically equivalent analogue of the enzyme could be a fusion protein which includes the catalytic site of the enzyme in a functional form, but it can also be a homologous variant of the enzyme derived from another species. Also, completely synthetic molecules that mimic the specific enzymatic activity of the relevant enzyme would also constitute "enzymatic equivalent analogues".

The term "industrial scale" relates to that the process is a large scale process suitable for industrial production. It is correlated to the requirement of the process, as described herein, that the chromatography column volume should be at least 5 L.

The term "rhPBGD containing extract" in relation to an extract obtained from a fermentation of a recombinant cell capable of expressing the rhPBGD denotes herein an extract derived from the fermentation.

The term "affinity chromatography" denotes the type of column chromatography, where the molecule to be purified is specifically and reversibly adsorbed by a complementary binding substance (ligand) covalently attached to an insoluble support (matrix). The sample is applied under conditions which favour its specific binding to the immobilized ligand. Unbound substances are washed away and the substance of interest can be recovered by changing the experimental conditions to those which favour its desorption.

The term "column volume of at least 5 L" relates to that the process, as described herein, is for industrial use and requires use of columns with a high volume. A volume of at least 5 L means that the column is capable of being filled with a packed gel comprising at least 5 L volume. When some of this loaded liquid is eluted more liquid may be loaded to the column.

The term "receiver" of step (v) of main aspect should be understood broadly. Depending on the requirement it may be a relatively large container or be a smaller box or a glass vial, etc.

Embodiment(s) of the present invention is described below by way of example(s) only.

DETAILED DESCRIPTION OF THE INVENTION

Recombinant Cell

The recombinant cell may be any recombinant cell suitable for recombinant production of rhPBGD. An example is prokaryotic cell, such as an *E. coli* cell or a *Bacillus* cell. An eukaryotic cell may be a yeast cell or a mammalian cell such as a Chinese Hamster Ovary (CHO). Alternatively, it may be a human cell.

Preferably it is a yeast cell and more preferably it is an *E. coli* cell.

For a detailed example of construction of a recombinant *E. Coli* cell reference is made to example 1 of WO01/07065 and for construction of recombinant HeLa cells and NIH 3T3 cells capable of expressing mouse rhPBGD reference is made to example 6 of WO01/07065.

Preferably, the fermentation is an industrial scale fermentation process, herein understood to encompass a fermentation process on a volume scale which is at least 300 L fermentation medium, preferably at least 500 L fermentation medium, more preferably at least 650 L fermentation medium, most preferably at least 800 L fermentation medium.

rhPBGD Containing Extract

Dependent on the specific type of recombinant cell and whether or not rhPBGD is secreted from the cell or not, the rhPBGD containing extract may be obtained in different manners cell known to the person of ordinary skill in the art.

For example, rhPBGD may be recovered from *E. coli* after fermentation by an extraction procedure involving for example ribipress, homogenisation, sonication, osmotic shock or total solubilization by detergent for example Tween 80, Triton X-100 or Brij. rhPBGD can be recovered from fermentation medium (if secreted) after production in yeast or from a total cellular extract using detergents such as Triton X-100, Tween 80 or Brij. Corresponding strategies may be employed from mammalian culture.

By use of standard techniques, it is within the skilled person's general knowledge to obtain rhPBGD containing extract from a fermentation of a recombinant cell.

For a detailed example of how to obtain a rhPBGD containing extract from a large scale fermentation of a recombinant *E. Coli* cell reference is made to example 7 of WO01/07065.

Affinity Chromatography Column

The process, as described herein, teaches that the first large scale chromatography column step should be an affinity chromatography column step.

There are a number of commercially available affinity chromatography columns, such as affinity coupling, group specific affinity, and metal chelate affinity columns.

The product catalogue 2001 of the company Amersham Pharmacia Biotech gives examples of affinity coupling columns such as columns comprising immobilising ligands containing —$NH_2$ and columns comprising ligands containing primary amino groups.

Metal chelate affinity columns are specially preferred for purifying proteins via metal ion complex formation with exposed histidine groups. Example 3 of WO01/07065 describes construction of a recombinant human Porphobilinogen deaminase with a "His-Tag" (rhPBGD-His). In order to purify rhPBGD-His according to the process of the present invention it is preferred to use a metal chelate affinity column, such as a column having a cobalt metal affinity resin.

In the present context in should be said that the purification working examples of WO01/07065 relating to purification of rhPBGD-His are all small scale processes (around 2 L fermentation) and they all use a DEAE ion exchange column as the first column step, and first thereafter apply a metal chelate affinity column. Furthermore as illustrated by comparing the outcome of a industrial large-scale purification performed according to the present invention (example 1) to the outcome of a large-scale purification performed according to WO01/07065 (example 3) the present invention have several surprising advantages. The surprising advantages are: 1) the serious precipitation problems with the first HIC step of the procedure in WO01/07065 is avoided; 2) the low yield were seen in the DEAE chromatography step of the large-scale purification performed according to WO01/07065, where most of the protein was lost, does not occur; and 3) the overall yield is significantly improved from very low (3.6 and 10.6% respectively) to approximately 30% (process 3).

Examples of group specific affinity columns are columns having porcine heparin as ligand or columns having Cibacron Blue 3G as ligand and using Triazine coupling as the ligand coupling method. A commercially available example of the latter is Blue Sepharose 6 Fast Flow (FF) from Amersham Pharmacia Biotech.

Example 1 herein provides a detailed description of a successful use of a Blue Sepharose 6 Fast Flow (FF) affinity column.

Accordingly, a preferred embodiment of the invention relates to the process, as described herein, wherein the affinity chromatography column of step (i) is a column using a triazine coupling as ligand coupling method, and more preferably wherein the ligand is Cibacron Blue 3G.

The formal chemical name of this ligand is 1-Amino-4-[[4-[[4-chloro-6-[[2(or 3- or 4-)-sulfophenyl]amino]-1,3,5-triazin-2-yl]amino]-3-sulfophenyl]amino]-9,10-dihydro-9,10-dioxo-2-anthracenesulfonic acid.

Based on common general knowledge and the description herein the skilled person is capable of choosing a specific affinity column, which he believes is useful in relation to purification of rhPBDG based on a specific rhPBGD containing extract.

Preferably, the column volume of the affinity chromatography column of step (i) has a column volume of at least 10 L, preferably at least 15 L, more preferably of at least 25 L, even more preferably of at least 30 L, and most preferably of at least 37 L or even more.

The Eluted Sample Comprising rhPBGD of Step (i)

As said above, an advantage of using an affinity chromatography column as the first large scale chromatography column step is that in one step the majority of the contaminants is removed. This provides a very pure rhPBDG containing sample which is suitable to work with in further large scale steps.

Accordingly, in a preferred embodiment the eluted sample of step (i) comprises rhPBGD in a purity where at least 60% by weight of the total protein in the sample is rhPBGD. More preferably at least 70% by weight of the total protein in the sample is rhPBGD, even more preferably at least 80% by weight of the total protein in the sample is rhPBGD, and most preferably at least 90% by weight of the total protein in the sample is rhPBGD. The percentage of rhPBGD is preferably measured by analytical HPLC according to manufacture protocol, e.g. by use of the commercially available analytical HPLC named Hewlett Packard or Agilent 1090 or 1100 in combination with an analytical column named Zorbax 300SB-CN from Rockland Technologies Inc.

Example 1 herein describes in detail a process where, after the affinity chromatography step, at least 90% by weight of the total protein in the sample is rhPBGD.

Chromatography Column Step (ii):

In principle this may also be an affinity chromatography step using a different type of affinity chromatography column as compared to the one used in step (i). However, it is preferred that the chromatography column of step (ii) is a column relying on a different principle than an affinity chromatography column.

The term "relying on a different principle" should in the present context be understood as that the column uses a different principle for separation of the compounds/molecules of interest. This is due to that the objective of step (ii) is to remove the non-wanted material, which was not removed during step (i). Non-wanted material may be non rhPBGD proteins derived from the fermentation, e.g. E. coli proteins if an E. coli recombinant cell was used. Examples of suitable columns are a hydrophobic interaction chromatography (HIC) column or a Ion-exchange chromatography (IEC) column.

Preferably, the chromatography column of step (ii) is an Ion-exchange chromatography column.

The term "Ion Exchange Chromatography (IEC)" should herein be understood according to the art as a column separating molecules such as proteins on the basis of their net charge at a certain pH by electrostatic binding to a charged group on the column. Ion exchange denotes the absorption of ions of one type onto a column in exchange for others which are lost into solution.

Examples of suitable IEC columns are columns such as a Q Sepharose column, a Q SP Sepharose column, or a CM Sepharose column. Preferably, it is a DEAE Sepharose column as used in working example 1 in order to remove E. coli proteins, which was not removed during the affinity chromatography step.

Preferably, the column volume of the chromatography column of step (ii) is having a column volume of at least 10 L, preferably of at least 15 L, more preferably of at least 25 L, even more preferably of at least 30 L, and most preferably of at least 37 L or even more.

Chromatography Column Step (iii):

According to the first aspect of the invention, this is an optional step.

As for step (ii), the objective of step (iii) is to remove the non-wanted material, which was not removed during the earlier steps.

Accordingly, a preferred embodiment relates to that the chromatography column of step (iii) is a column relying on a different principle than an affinity chromatography column and also relying on a different principle than the column used in step (ii).

Preferably, the chromatography column of step (iii) is a hydroxyapatite column, more preferably a ceramic hydroxyapatite column.

Hydroxyapatite $(Ca_5(PO_4)_3OH)_2$ is a form of calcium phosphate that can be used for the separation and purification of proteins, enzymes, nucleic acids, viruses, and other macromolecules. Ceramic hydroxyapatite is a spherical, macroporous form of hydroxyapatite. CHT Type I (Bio-Rad) is an example of a suitable commercially available ceramic hydroxyapatite chromatography column. Example 1 herein describes use of this column in step (iii).

Formulating the Sample to get a Sample Comprising the rhPBGD in a Suitable Formulation Buffer The objective of this step is to get the sample in a suitable formulation buffer. Preferably, the purified rhPBGD is desalted by exchange with formulation buffer to an acceptable concentration. See example 1 herein for further details.

As illustrated in Example 4 the rhPBGD is non-toxic to human beings and suitable for clinical applications thus a significant embodiment of the present invention is a pharmaceutical composition comprising rhPBGD obtainable by the process disclosed here. The composition comprising rhPBGD may further comprise one or more excipient(s) or carrier(s) and the composition may be in solid form or in liquid form.

In one embodiment the composition comprises a diluent selected from the group consisting of aqueous carriers, water (e.g. Water For Injection/WFI), buffered water, saline (e.g. 0.4% saline), glycine (e.g. 0.3% glycine) and diluents that contain one or more salts, such as a calcium salt (e.g. $CaCl_2$) or a combination of a sodium and a calcium salt (e.g. NaCl and $CaCl_2$). In particular a diluent which is the buffer: Sodium $HPO_4$ (3.67 mM), Glycine (27 mM), Mannitol (250 mM), Water for injection (WFI) qs.; pH 8.0±0.5, is preferred.

The composition my further comprise one or more therapeutically active agents.

Yet another significant application of the present invention is the use of a rhPBGD for the manufacture of a medicament capable of producing a relative reduction in plasma PBG concentration of human AIP patients of more than 50%, even more preferably more than 60%, still more preferably more than 70%, even more preferably more than 80% and most preferably at least 90% within 10 minutes from the time of a dose of at least 0.1 mg rhPBGD/kg injected intravenously.

As illustrated in example 3 more doses is clinically acceptable and able to produce a significant reduction in plasma PBG concentration. Thus in an important embodiment of the present invention is the use of a rhPBGD for the manufacture of a medicament capable of producing a relative reduction in plasma PBG concentration of human AIP patients of more than 50%, which is obtained by an intravenous injection of a dosis of rhPBGD ranging from 0.1 to 2 mg rhPBGD/kg, preferably from 0.1 to 1 mg rhPBGD/kg, more preferably from 0.25 to 1 mg rhPBGD/kg and most preferably from 0.5 to 1 mg.

It is well known that the PBG levels are increased in AIP patients. Consequently it is presumed that a lowering of the PBG plasma levels may be beneficial to AIP patients and other patients suffering from increased PBG levels in plasma. Therefore a particular useful embodiment of the present invention is a method of treating a person in need thereof by administering to said person a rhPBGD obtainable by the process according to the present invention and thereby obtaining a relative reduction in plasma PBG concentration of the person of more than 50%, even more preferably more than 60%, still more preferably more than 70%, even more preferably more than 80% and most preferably at least 90% within 10 minutes from the time an effective amount of rhPBGD is given.

The invention is further illustrated by the following non-limiting examples.

EXAMPLE 1

Industrial Process for Purification of Recombinant Human Porphobilinogen Deaminase (rhPBGD)

Introduction

Below is described several large-scale manufacturing purification processes for rhPBGD. The processes isolate the several rhPBGD species as a single group from the heterogeneous cell lysate. This crude extract includes the rhPBGD enzyme species as well as other proteins, DNA/RNA and related by-products, endotoxins and metabolites (e.g. heme-related metabolites) etc. from the E. coli host, which are removed by the purification process.

Three processes are described. Process 1 which comprises step I, II, III, V and VI. Process 2 is an expanded process that includes step IV to reduce the level of host E. coli proteins (ECP) level in order to obtain material suitable for clinical studies. Process 3 is similar to process 2 except that the amount of material loaded relative to the amount of Blue Sepharose 6FF is different.

An outline of the purification process is given in FIG. 1.

The purification process comprises the following steps:

I. fermentation product: Crude frozen rhPBGD extract (≈150 Kg with ≈7.5 mg total protein/mL) is thawed and stored in a cooled tank (<+10° C.) under nitrogen before use. The extract is diluted with water just prior to loading on a Blue Sepharose column.

II-1. Blue Sepharose affinity Chromatography: Chromatography at pH 7.3 on 40 L Blue Sepharose 6FF packed in a 45 cm diameter column in process 1 and 2. In process 3 the Blue Sepharose affinity Chromatography is performed at pH 7.3 on 80 L Blue Sepharose 6FF packed in a 60 cm diameter column or alternatively the extract could be divided in two equal pools and chromatographed on a 40 L Blue sepharose 6FF packed in a 45 cm diameter column in two consequtive runs. The two separate eluates are then pooled before dilution (alt. Diafiltration) and loading onto the DEAE sepharose column.

II-2. Dilution or diafiltration (tangential flow filtration; TFF): of Blue Sepharose pool to reduce conductivity before binding product to DEAE Sepharose.

III. DEAE Sepharose: Chromatography at pH 7.6 on 30 L DEAE Sepharose FF packed in a 40 cm diameter stainless steel column (or 45 cm diam. glass column).

IV. Ceramic Hydroxyapatite (CHT): Stepped chromatography of DEAE Sepharose pool at pH 7.6 and pH 7.9 on 16 L CHT (Type 1, 40 µm) packed in a 45 cm diameter glass column. DEAE Sepharose pool applied directly to CHT. This CHT step is added to the purification process to obtain rhPBGD intended for clinical testing: Process 2.

V. Diafiltration(TFF)/Formulation on Millipore ultrafiltration system: DEAE Sepharose or CHT pool diafiltered (tangential flow filtration; TFF) against formulation buffer pH 7.5–8.5 using Millipore Pellicon 2 cartridge with Biomax 10 V-screen (1 or 2 m2).

VI. Controlled bio-burden filling: Filtration of TFF pool through sterile 0.2 µm filter into sterile 1000 ml Nalgene containers in a LAF hood.

1. The rhPBGD Containing Extract.

The rhPBGD containing extract was obtained from a large scale fermentation (850 L fermentation medium) of an *E. coli* recombinant cell capable of expressing the rhPBGD.

The manufacturing scale purification process for rhPBGD is based on production strain PBGD-2. PBGD-2 is a hemC-deleted *E. coli* JM105-H-R6 transformed with the expression plasmid pExp1-M2-BB to yield the final production strain PBGD-2 which is free from production of PBGD of non-human origin. PBGD-2 was deposited under the Budapest Treaty on 9 Jul. 1999 with DSMZ (Deutsche Sammiung von Mikroorganismen und Zellkulturen, GmbH, Mascheroder Weg 1b, D-38124 Braunschweig, Germany) under the accession No. DSM 12915. Construction of the *E. coli* recombinant cell is described in WO01/07065.

The large scale fermentation process is described in detail in example 7 of WO01/07065. After fermentation the product is homogenised, cell debris is removed, the product is membrane filtered, frozen at −20° C. in 20 L Flexiboy bags filled to 10 L and kept at −20° C. until thawing.

2. General Considerations on Stability.

Although the apoenzyme appears to be denatured relatively easily, the holoenzyme forms are more stable. For example the latter are unusually heat stable; at concentrations >1 mg/mL no enzymatic activity is lost by incubation at 56° C. for 2 h, and at 60° C. for 2 h<10% is lost. One published isolation method heat-treats the lysate at 80° C. for 50 min without loss of PBGD activity (Smythe and Williams, 1988). Therefore, periods up to 24 h at room temperature during processing, for example, are well tolerated, but beyond that, activity is gradually lost (e.g. loss of ≈70% after 1 week). While purification is in progress the product is kept chilled at <10° C. under nitrogen (minimises air oxidation) as much as is practicable.

3. Details of the Large-Scale Process

Setting up for Production

Procedures were introduced to prepare the facility's equipment and systems before each production run. Thus all systems and ancillary pipelines are cleaned in place (CIP) or steamed in place (SIP) and sanitised according to acceptable procedures. The analytical HPLC, pH meter and conductometer instruments, as well as the in-line mixing pump (for in-line dilution), LPLC system pH meter, Conductometer, UV (280 nm) and recorder are prepared (with adjustments as required) and in-line filter housings with replacement filter cartridges (e.g. 0.2, 1, 3, 5 μm filters) made ready; the filters are used in-line to minimise bio-burden and particulates in all solutions during chromatography and diafiltration. When required, the chromatography columns and UF are coupled to the LPLC system, and the UF Biomax 10 V membranes and the chromatography resins are equilibrated. Chromatography and diafiltration are carried out in clean room conditions.

Buffers are prepared for the purification steps when required, using a common buffer preparation tank. Purified water/WFI and all buffers are transferred under nitrogen gas pressure via microbial retentive filters (0.2 μm) and stainless steel pipelines to holding tanks in the purification suite.

Step I. Fermentation Product—Thawing/Dissolution of Crude rhPBGD

Crude frozen extract in 20 L capacity Flex Boy bags (each holding 10 Kg extract at about 7.5 mg total protein/mL) is stored at −20° C. after delivery until required or is thawed immediately. Frozen extract (150±50 Kg) containing 1–1.3 Kg total protein is thawed for up to 48 h at room temperature then placed into cold storage at 2–8° C. (up to 1 week) for final melting of residual ice. The thawed solution from each bag is transferred to a cooled 250 L tank (2–8° C.) before loading the Blue Sepharose affinity chromatography column. The solution is mixed gently and a sample taken for analytical tests. The solution can be prepared 1 day ahead and kept at <5° C. under a nitrogen atmosphere; e.g. 0.5 Bar in the tank. Product purity is normally 40–50% according to HPLC analysis. If two separate blue columns are run, only half of the bags are thawn at a time.

Step II. Blue Sepharose Affinity Chromatography

Purpose.

The extract usually contains 20–40% expressed rhPBGD enzyme with 60–80% unknown host by-products, including host *E. coli* proteins (ECP) and DNA. Affinity chromatography is used for rapid initial clean up of the target rhPBGD group from the crude source material. Here the enzyme is captured, concentrated and stabilised by bulk removal of most contaminants. Other contaminants are removed during later process steps.

Step II-1:Chromatographic Process:

Prior to chromatography, the Blue Sepharose column is set up and equilibrated. Use in-line 3 or 5 μm pre-filter and ≤1 μm column guard filter to remove particles/precipitates from solutions, and use air trap before column inlet. Use upward flow in all steps. The crude extract is loaded onto a 40 L resin bed after dilution with purified water.

Resin: Blue Sepharose 6FF from Amhersam Pharmacia Biotech (APB)

Resin Bed Volume: 40±5 L (bed height 25±3 cm; BPG-450 glass column, 45 cm diam. from APB) if run in 2 batches. If run in one batch: 80±5 L (bed height 28±2 cm, 60 cm diam. column)

Equilibrate with 4–6 CV of 10 mM potassium phosphate buffer, pH 7.3±0.2, using upward flow. Check pH in column outlet.

Operational flow rate 0.7–2.4 L/min. (volumetric) or 25–90 cm/h (linear).

Batch Load: 5.0–5.5 g rhPBGD or 17±5 g total protein load/L resin bed. The current operational condition is 350–450 g rhPBGD contained in 1–1.3 Kg total protein in 140–180 Kg (operationally, Kg assumed to be L) crude extract (at ≈7.5–8.5 mg total protein/mL before in-line dilution) loaded onto a 75–85 L resin bed or half load onto a 35–45 L resin bed (repeated 2 times in series). Since the specified total protein range of the extract is 4.5–10 mg/mL then volume loads of 195±90 Kg crude extract could apply.

Wash 1: 2–3 CV of 10 mM potassium phosphate buffer pH 7.3±0.2. Upward flow.

Wash 2: 2–3 CV of 10 mM potassium phosphate buffer pH 7.3±0.2+75 mM KCl (9–12 mS/cm; not to exceed 15 mS/cm. conductivity). Upward flow.

Elution: 2–3 CV of 10 mM potassum phosphate buffer pH 7.3±0.2+300 mM KCl.

Conductivity 30–40 mS/cm. Anticipated yield 200±50 g rhPBGD assuming 50% binding, with full recovery of that bound. HPLC purity to be ≧90%.

Store the rhPBGD product in a chilled tank (<+10° C.) under nitrogen.

In-process analytical tests of the enzyme pool and other analytical tests for obtaining additional relevant documentation are done.

Step II-2: Dilution or Diafiltration

Purpose.

This step is used simply to reduce the concentration of salts to a suitable conductivity (<10 mS/cm) that allows binding of the captured rhPBGD to the DEAE Sepharose resin in the succeeding ion exchange chromatography step.

Process.

Dilution is obtained by addition of purified water directly or by ultrafiltration against purified water. In the present example the eluent from the Blue Sepharose step is loaded by in-line dilution onto a 30 L resin bed (see Chromatographic Process in step III).

Step III. DEAE Sepharose FF ion Exchange Chromatography (IEC)

Purpose.

This stage of the purification process essentially combines "intermediate purification" and "polishing". It is used to remove residual contaminants, especially host E coli proteins (ECP) and DNA, and allows the selective group adsorption and elution/concentration of the captured rhPBGD species. Here, further removal of trace contaminants to obtain enzyme end product of required high-level purity for toxicology studies occurs (Process 1). However, an extra chromatographic polishing step (CHT Ceramic Hydroxyapatite—step IV) that removes residual, host ECP and DNA even ore efficiently has been assessed for producing clinical material (Process 2).

Chromatographic Process.

Prior to chromatography the DEAE Sepharose column is set up and equilibrated. Use in-line 3 or 5 µm pre-filter and ≦1 µm column guard filter to remove particles/precipitates from solutions, and use air trap before column inlet. Use upward flow in all steps. The product eluent from the Blue Sepharose step is loaded by in-line dilution onto a 30 L DEAE resin bed. Here the product conductivity is adjusted to 5–7 mS/cm (aiming for about 5 mS/cm) by in-line mixing (dilution) with purified water to allow binding of product on the resin. In-line dilution and filtration allows direct loading on the DEAE Sepharose without needing to desalt by ultrafiltration. Loads of 200±50 g were aimed for.

Resin: DEAE Sepharose FF from Amhersam Pharmacia Biotech (APB)

Resin Bed Volume: 30±5 L (bed height 24±4 cm; Dan-Process 400 column, 40 cm diam)

Pre-equilibrate the DEAE Sepharose with 6–7 CV of 100 mM potassium phosphate buffer pH 7.6±0.3.

Equilibrate with 5–7 CV of 10 mM potassium phosphate buffer pH 7.6±0.3 until pH and conductivity are acceptable (pH 7.5±0.4; Cond. <4 mS/cm).

Operational flow rate: 1.6–2.1 L/min. (volumetric) or 75–100 cm/h (linear). Upward flow.

Batch Load: The rhPBGD product from the Blue Sepharose step (200±50 g in 50–80 L) is mixed by in-line dilution with purified water (1 product+5 water v/v) and loaded onto the DEAE Sepharose column. Conductivity should be kept in the range 5–7 mS/cm (aiming for about 5 mS/cm) for proper binding. Flow rate 1–1.6 L/min during loading.

Flow rate: 1.6–2.1 L/min for washing and elution.

Wash: 6–7 CV of 10 mM potassium phosphate buffer pH 7.6±0.3; conductivity <4 mS/cm.

Elution: 2–3 CV of 10 mM potassium phosphate buffer pH 7.6±0.3+100 mM KCl; conductivity 11–14 mS/cm Product should elute in 50–80 L. Anticipated yield: 190±45 g rhPBGD (assuming 90%), HPLC purity ≧97%.

Store the rhPBGD product in a chilled tank (<+10° C.) under nitrogen.

In-process analytical tests of the enzyme pool and other analytical tests for additional relevant documentation are performed (see table 4).

Step IV: Ceramic Hydroxyapatite (CHT) Chromatography

Purpose.

This step is included in the final process for clinical production—Process 2—to reduce host E. coli proteins (ECP) levels. Two different gels were initially tested with good results, CHT-I, 40 µm and CHT-II, 40 µm. CHT-I was chosen mainly because of its higher binding capacity. Note that with the introduction of CHT-I after ion exchange chromatography (IEC) to reduce ECP levels from 0.1–0.5 µg/mg to <10 ng/mg.

Chromatographic Process.

Prior to chromatography the CHT column is set up and equilibrated. Use in-line 3 or 5 µm pre-filter and <1 µm column guard filter to remove particles/precipitates from solutions, and use air trap before column inlet. Flow direction is always downward during this step, since the gel structure is not suitable for upward flow. The product eluent from the DEAE Sepharose step is loaded directly onto a 16–18 L resin bed when conductivity is 5–10 mS/cm (alternatively it is mixed in-line with water to a conductivity between 5–10 mS/cm). Working solutions were developed, comprising 10 mM potassium phosphate buffer pH 7.6±0.2, with and without KCl (150 mM) for column equilibration and washing and with 400 mM KCl for product elution. Loads of 135±45 g were aimed for.

Resin: Ceramic hydroxyapatite gel, CHT type I, 40 µm (BioRad)

Resin Bed Volume: 16±2 L (bed height 10±1.5 cm; BPG-450 glass column, 45 cm diam. from APB). DEAE Sepharose pool applied directly to CHT.

Equilibration: 3–5 CV of 10 mM potassium phosphate buffer pH 7.6 ±0.2.

Operational flow rate: 30–95 cm/h (linear), or 0.8–2.5 L/min. (volumetric).

Sample loading: rhPBGD product (135±45 g) from the DEAE sepharose step at between 5–10 mS/cm conductivity is loaded onto the CHT column.

Washing and elution: Initial settings used in clinical production 1 (Clin 1)

Wash 1: 2–3 CV of 10 mM potassium phosphate buffer pH 7.6±0.2

Wash 2: 2–3 CV of 10 mM potassium phosphate buffer pH 7.6 ±0.2+150 mM KCl

Elution: 3–4 CV of 10 mM potassium phosphate buffer pH 7.6±0.2+450 mM KCl.

The rhPBGD purity is normally >98% as determined by HPLC.

Washing and elution: Modified and final settings used in clinical production 2 (Clin 2)

Wash: 4–5 CV of 10 mM potassium phosphate buffer pH 7.6±0.2+50 mM KCl; conductivity 7–10 mS/cm Elution: 2–4 CV of 25 mM potassium phosphate buffer pH 7.9 ±0.1+250 mM KCl; conductivity 30–40 mS/cm. Product should elute in 30–50 L Anticipated yields: 115±40 g rhPBGD (assuming 85%), HPLC purity >98%.

Store the rhPBGD product in a chilled tank (<+10° C.) under nitrogen.

In-process analytical tests of the enzyme pool and other analytical tests for additional relevant documentation are done.

Washing and elution: Modified and final settings used Process 3 (2×Blue)

After storage, wash the resin free of buffered ethanol with 1–2 CV's of water Pre-equilibrate: 3–5 CV's of 0.4 M potassium phosphate buffer pH 7.6±0.2 (pH in outlet must be <7.8)

Equilibration: 3–5 CV of 10 mM potassium phosphate buffer pH 7.6 ±0.2.

Wash: 4–5 CV of 10 mM potassium phosphate buffer pH 7.6±0.2+50 mM KCl; conductivity 7–10 mS/cm Elution: 5–6 CV of 25 mM potassium phosphate buffer pH 7.9±0.1+250 mM KCl; conductivity 30–40 mS/cm. Product should elute in 30–50 L Anticipated yields: 180±40 g rhPBGD, HPLC purity >98%.

Store the rhPBGD product in a chilled tank (<+10° C.) under nitrogen.

In-process analytical tests of the enzyme pool and other analytical tests for additional relevant documentation are done.

Step V: Diafiltration (TFF)/Formulation on Millipore Ultrafiltration System

Purpose.

Ultrafiltration, involving concentration and diafiltration (as tangential flow filtration; TFF), is used to remove potassium salts and any residual low molecular weight metabolites, and for final washing/concentration by exchange with formulation buffer that contains enzyme stabilisation additives in water for injection (WFI).

Ultrafiltration Process (As Tangential Flow Filtration; TFF).

Before TFF the Ultrafiltration system (UF) is set up and equilibrated with formulation buffer. The product eluent from the ceramic hydroxyapatite step is pumped through the UF at 20 L/min feed cross-flow. During processing the product is maintained <15° C. by cooling of the feed tank. The volume of retentate is reduced to 20–30 L and diafiltration is continued for 8–12 volume exchanges (200–250 L in case of Process 1 or 300–350 L in case of Process 2 and 200–300 L in case of Process 3) of formulation buffer. Solution pH, Conductivity and Osmolality are monitored. The product is concentrated further and the conductivity is reduced to <1 mS/cm. Extra formulation buffer is used to adjust rhPBGD concentration and solution osmolality (to isotonicity) to meet specifications.

UF Membranes: Millipore Biomax 10 V screen (10 kDa cut off), 2×0.5 m$^2$ or with 2 m$^2$.

TFF: Feed flow rate 1–1.5 m$^3$/h, permeate flow rate 50–60 L/h to give permeate cross-flow of 20 L/min.

Working volume range: 10–80 L (adaptation of UF system S11). Input: 135±45 g rhPBGD (Process 1) or 115±40 g (Process 2), at ≧95% purity, in 60–80 L.

Formulation buffer: Sodium HPO$_4$ (3.67 mM), Glycine (27 mM), Mannitol (250 mM), Water for injection (WFI) qs.; pH 8.0 ±0.5

Anticipated yields: Process 1; 115±40 g rhPBGD (Process 2: 100±35 g) in 15±5 L retentate (to obtain 7.5±2.5 mg/ml solution) at pH 8.0±0.5, osmolality 250–350 mOs/Kg and conductivity <1.0 mS/cm.

Step VI: Controlled Bioburden Filtration and Filling

Purpose.

This is essentially the last purification step in the process prior to transferring the product to the filling facility. Its purpose is to obtain the product with a low bio-burden (aseptic rhPBGD).

Process.

The concentrated rhPBGD solution is transferred under nitrogen gas pressure (0.5–1.5 Bar) through clean pipelines, flow manifold and filter train from the LAF area in the Clean room to the Class 100 LAF bench into sterile containers for subsequent freezing and transport. The filter train comprises a 3–5 μm guard filter and 0.2 μm sterile filter to reduce the bacterial count to <10 cfu/mL. Samples are taken for the battery of analytical tests (see table 4 and 5) before freezing. After meeting the required specifications the frozen product is released and transported to a third party where it is prepared to the precise rhPBGD concentration required and after passage through another 0.2 μm filter is filled into vials.

4. Results

The serial yields of rhPBGD for all production runs involving Process 1 and Process 2 (Test 1, Test 2, Tox 1, Tox 2, Clin 1, Clin 2, Clin 3 and Clin 4) during the purification process are summarized in Table 1 that follows. On average, the final outcome was about 77 g (range 41–106 g). Theoretical evaluation of yields of Process 3 (2×Blue) compared to Process 2 is presented in Table 6 and the actual results from Process 3 are summerized in Tables 7 and 8. Batch HB001E3 (Table 7) was a test run and due to some problems in the DEAE and CHT steps some process changes were made for production batch HB001E4 (Table 8). This is also reflected in the higher yield for HB001E4 (148 g according to HPLC analysis relative to standard) compared to HB001E3 (118 g according to HPLC analysis relative to standard). In conclusion: The improvements in process 3 compared to process 2 resulted in significively higher yield with the same or better quality of the final product.

As deduced from the Process 1 and Process 2 data in Table 1 an average rhPBGD recovery was 130 g (range 117–148 g) or about 33% was obtained in the Blue Sepharose capture step (also see Tables 2 and 3). The overall efficiency for Process 1 is about 22% (Table 2). A similar efficiency (20%; Table 3) was obtained in Process 2, which included an extra chromatography step. Process 3 resulted in an recovery of 200–203 g from the Blue sepharose or 42–45% which is a significant improvement compared to process 2.

The results from Test 2, Tox 1 and Tox 2 showed that the purification conditions developed for Process 1 could achieve the objectives of approximately 100 g product at >90% HPLC purity from 100–300 L of crude rhPBGD extract, containing 1–1.5 Kg total protein (300–450 g rhPBGD). The purified rhPBGD in both Tox batches met the required analytical specifications (Table 4). ECP levels, however, ranged from 100–200 ng/mg protein making development of Process 2 obligatory for clinical purposes.

Compared with Process 1 the ECP level in the final product was reduced from 100–200 ng/mg protein essentially to 10 ng/mg for Process 2, i.e. some 10-fold reduction (Tables 5). There was at least a 70,000-fold reduction during the purification from crude starting material to finished product as represented by Clin 2, substantially by the Blue Sepharose step. The DNA levels also decreased substantially, e.g. from 30,000 pg/mg rhPBGD in the crude starting material to 4–11 pg/mg rhPBGD in the final product (Table 5). The ECP level for HB001E3 (Process 3) were <3.2 ng/mg and DNA was 59 pg/mg. The EPC level for HB001E4 was <3.2 ng/mg and DNA was 36 pg/mg.

TABLE 1

Serial yields of rhPBGD during the purification process - Summary of Process 1 and Process 2 production runs

| Process Step | Test 1 HB005C Amount (g) | Test 2 HB006C Amount (g) | Tox 1 HB007C Amount (g) | Tox 2 HB008C Amount (g) | Clin 1 HB001D1 Amount (g) | Clin 2 HB002D1 Amount (g) | Clin 3 HB002D2 Amount (g) | Clin 4 HB001D2 Amount (g) |
|---|---|---|---|---|---|---|---|---|
| Crude rhPBGD Load | | | | | | | | |
| (i) Total protein | 924 | 1058 | 1400 | 1292 | 1150 | 1352 | 1168 | 1040 |
| (HPLC purity) | ≈48% | ≈48% | ≈39% | ≈39% | 41% | 46% | 45% | ≈48% |
| (ii) rhPBGD @ 30 ± 10% | 277 ± 92 | 315 ± 103 | 420 ± 140 | 388 ± 129 | 345 ± 115 | 406 ± 135 | 350 ± 117 | 312 ± 104 |
| (iii) rhPBGD[1] | 326 | 401 | 582 | 532 | 369 | 492 | 420 | 390 |
| rhPBGD if taken as Mean | 302 | 358 | 501 | 460 | 357 | 449 | 385 | 351 |
| Blue Sepharose[1] | 136 | 148 | 138 | 124 | 117 | 122 | 135 | 124 |
| HPLC purity | 95% | >98% | 98.9% | >99% | 95% | >97% | 95% | >95% |
| Tangential flow filtration (TFF)[1] | 115 | Nip[2,3] | Nip[2,3] | Nip[2,3] | Nip[2,3] | Nip[2,3] | Nip[2,3] | Nip[2,3] |
| DEAE Sepharose[1] | 114 | 127 | 104 | 111 | 116 | 113 | 124 | 100[4] |
| HPLC purity | 98% | >99% | >99% | >99% | >99% | >99% | >99% | >98% |
| Ceramic Hydroxyapatite[1] | Nip[2,3] | Nip[2,3] | Nip[2,3] | Nip[2,3] | 99 | 105 | 111 | 101 |
| HPLC purity | | | | | >99% | >99% | >99% | >99% |
| TFF/Formulation/ 0.2 μm filtration[1] | 63 | 100 | 82 | 106 | 41[6] | 84 | 70 | 72 |
| HPLC purity | >96% | 98.3% | >98.5% | >99% | >99% | >99% | >99% | 98.8% |

Notes:
[1]rhPBGD adjusted to BCA protein method. 2. Nip means "Not in process".
[3]Process 2° used for Test 2, Tox 1 and Tox 2. Process 2 used for Clin 1, Clin 2, Clin 3 and Clin 4. 4. Underestimate; technical error.
[5]No intermediate sampling possible (no bottom sampling port; added for Clin 2 and later runs of Process 2). UF technical failure in this case, trapped a substantial amount of product.

TABLE 2

Efficiency of process steps (Process 1): (Average Progressive Yields of rhPBGD from Test 2, Tox 1 and Tox 2)

| | | % Yield of rhPBGD: | |
|---|---|---|---|
| Process Step | Amount (g) | Relative to start | Relative to prior step Mean |
| Crude Load (Start) | | | |
| Total protein (HPLC purity) | 1250 42% | | |

TABLE 2-continued

Efficiency of process steps (Process 1):
(Average Progressive Yields of rhPBGD from Test 2, Tox 1 and Tox 2)

| | | % Yield of rhPBGD: | | | | | |
|---|---|---|---|---|---|---|---|
| | Amount | Relative to start | | | Relative to prior step | | |
| Process Step | (g) | | | | | | Mean |
| rhPBGD (as 30 ± 10% of total) | 374 ± 124 | 100 | 100 | 100 | 100 | 100 | 100 |
| rhPBGD[1] | ≈505 | | | | | | |
| Blue Sepharose | 137[1] | 37 | 27 | 32 | 37 | 27 | 32 |
| (HPLC purity) | >98% | | | | | | |
| DEAE Sepharose | 114[1] | 30 | 23 | 26 | 83 | 83 | 83 |
| (HPLC purity) | >99% | | | | | | |
| Ceramic Hydroxyapatite (CHT)[2] | Nip[2] | Nip[2] | Nip[2] | Nip[2] | Nip[2] | Nip[2] | Nip[2] |
| (HPLC purity) | | | | | | | |
| Diafiltration (TFF) to 2 μm | 96 | 26 | 19 | 22 | 84 | 84 | 84 |
| filtration (HPLC purity) | >98% | | | | | | |

Notes
[1] Relative to reference rhPBGD determined by BCA protein method.
[2] Nip: CHT is not in process 1.

TABLE 3

Efficiency of process steps (Process 2):
(Average Progressive Yields of rhPBGD from Clin 1, 2, 3 and 4)

| | | % Yield of rhPBGD: | | | | | |
|---|---|---|---|---|---|---|---|
| | Amount | Relative to start | | | Relative to prior step | | |
| Process Step | (g) | | | | | | Mean |
| Crude Load | | | | | | | |
| Total protein | 1178 | | | | | | |
| (HPLC purity) | ≈44% | | | | | | |
| rhPBGD (as 30 ± 10% of total) | 353 ± 118 | 100 | 100 | 100 | 100 | 100 | 100 |
| rhPBGD[1] | ≈420 | | | | | | |
| Blue Sepharose | 124[1] | 35 | ≈30 | ≈32.5 | 35 | ≈30 | ≈32.5 |
| (HPLC purity) | ≧95% | | | | | | |
| DEAE Sepharose | 113[1] | 32 | 27 | ≈30 | 91 | 91 | 91 |
| (HPLC purity) | >98% | | | | | | |
| Ceramic Hydroxyapatite | 104[1] | 29.5 | 25 | ≈27 | 92 | 92 | 92 |
| (HPLC purity) | >99%[6] | | | | | | |
| Diafiltration (TFF) to 0.2 μm | ≈"67"[1] | 19 | 16 | ≈18 | 64.5 | 64.5 | 64.5 |
| filtration | (75)[2] | (21) | (18) | ≈20 | (72)[3] | (72)[3] | (72) |
| (HPLC purity) | >99% | | | | | | |

Notes
[1] Relative to reference rhPBGD determined by BCA protein method.
[2] Excludes Clin 1 data, in which higher than normal loss at the TFF was experienced.
[3] Process efficiency factor (rel. to load from prior step): 1 × 0.325 × 0.91 × 0.92 × 0.72 ≈0.2 (≈ 1 × 0.35 × 0.9 × 0.9 × 0.7).

TABLE 4

Process 1 - Analytical data of bulk rhPBGD drug substance for Toxicology studies

| TEST | METHOD NO. | SPECIFICATION LIMIT | RESULTS Tox. No 1 | RESULTS Tox. No 2 |
|---|---|---|---|---|
| Content | | | | |
| rhPBGD specific activity (Units/mg) | E 001:2 | >10 | 25.5 | 27.0 |
| rhPBGD protein concentration (mg/mL) | P 001:2 | >5 | 8.04 | 7.8 |
| Identity | | | | |
| Retention time of main peak on HPLC (relative to standard) | R 001:1 | Approved | Conforms | Conforms |
| Purity | | | | |
| HPLC (% main peak) | R 001:1 | >90% | >98% | >99% |
| *E. coli* proteins (ECP) (µg/mg protein) | E 005:1 | <5 | 0.11 | 0.105 |
| DNA (ng/mg protein) | D 002:0.1 | For info | ND | ND |
| Other Tests | | | | |
| Bacterial count (cfu/mL) | Ph.Eur. | <10 | <1 | <1 |
| LAL (IU/mL) | Ph.Eur./USP | <25 | 10.5 | 8.52 |
| Osmolality (mOs/kg) | Ph.Eur. | 250–350 | 270 | 270 |
| pH | Ph.Eur. | 7.5–8.5 | 7.7 | 7.66 |
| Potassium (ppm) | Atomic abs. | For info | <10 | <50 |
| Blue matrix leak (620 nm) | Abs | For info | <5 | <6 |
| (nmol/mL) | | | 0.44 | 0.74 |
| (nmol/mg) | | | | |

TABLE 5

Process 2 - Analytical data of bulk rhPBGD drug substance for Clinical (or Toxicology) studies.

| TEST | METHOD NO. | SPECIFICATION LIMIT | RESULTS Clin. No 1[1] | 2 | 3 | 4 |
|---|---|---|---|---|---|---|
| Content | | | | | | |
| rhPBGD specific activity (Units/mg) | E 001: 2 | 15 | 20.1 | 21.3 | 22.4 | 21.7 |
| rhPBGD protein concentration (mg/mL) | P 001: 2 | 6 | 3.0[1] | 8.4 | 8.4 | 6.6 |
| Identity | | | | | | |
| Retention time of main peak on HPLC (relative to standard) | R 001: 1 | Complies (C) | C | C | C | C |
| Purity | | | | | | |
| HPLC (% main peak) | R 001: 1 | >90% | 100 | 100 | 100 | 100 |
| *E. coli* proteins (ECP) (ng/mg protein) | E 005: 1 | 100 | <1.8 | 10 | 10 | 11 |
| DNA (pg/mg protein) | D 002: 0.1 | For info | ND | 4 | 16 | <7 |
| Other Tests | | | | | | |
| Bacterial count (cfu/mL) | Ph.Eur. | 10 | <1/5 mL | 1/5 mL | <1/10 mL | <1/10 mL |
| LAL (IU/mL) | Ph.Eur/USP | 25 | 1.27 | 8.9 | 5.42 | 1.22 |
| Osmolality (mOs/kg)[2] | Ph.Eur. | 250–350 | 272 | 255 | 291 | 287 |
| pH[2] | Ph.Eur. | 7.5–8.5 | 7.7 | 7.5 | 7.6 | 7.6 |
| Potassium (mmol/L) | Atomic abs. | <3.2 | <0.25 | 0.5 | 0.41 | 0.35 |
| Blue matrix leak (nmol/mL) | Abs (620 nm) | For info | <3.5 | 0 | <1 | <1.2 |

Notes:
ND = Not determined
[1] Except for the protein concentration in Clin 1 the analytical results for all four batches were within nominal specifications. Consequently three batches, Clin 2, Clin 3 and Clin 4, were approved for clinical (and toxicology) studies, while Clin 1 was approved for toxicology studies only. In some respects the protein analyses determined externally differed slightly from the values determined from processing.
[2] Both Osmolality and pH tended to be on the low side of the specification so it was recommended to make slight adjustments to the formulation buffer composition to ensure the final osmolality and pH were closer to 300 mOs/kg and pH 8.0, respectively.

TABLE 6

Predicted end yields after capture of rhPBGD on Blue Sepharose Comparison of current 1 × 40 L Blue Sepharose column with prediction for 2 × 40 L Blue Sepharose columns using 1.3 Kg of total protein in crude rhPBGD starting material

| | Blue Sepharose column | |
|---|---|---|
| rhPBGD Capture | 1 × 40 L Current method | 2 × 40 L or 80 L Modified method |
| Load of total protein (g, or Kg) | 1.3 Kg | 1.3 ± 0.1 Kg |
| rhPBGD @ 30% (g) | 390 | 400* |
| As current 35% (30–40%) capture (g) | 136 | |
| Projecting 55% (50–60%) capture (g) | | 220 |
| Probable or predicted end yield: | | |
| (i) current method basis (g) | 77 | 125* |
| (ii) with improved TFF recovery (g) | | (140)* |
| Concentrated volume from TFF: | | |
| UF | 4–6 L | 4–6 L |
| T02 feed tank | 0–2 L | 5–15 L |
| UF flush | 3–6 L | 3–6 L |
| Total end volume | 10–13 L | 15–23 L |
| Desired rhPBGD concentration (mg/mL) | 6–8 | 6–8 |

*Notes:
A rational working hypothesis would be that 1.3 ± 0.1 Kg (as 2 × 650 ± 50 g) contains ≈400 g rhPBGD and after serial purification by (i) Blue Sepharose chromatography, (ii) DEAE Sepharose chromatography, (iii) CHT chromatography, (iv) TFF and (v) 0.2 μm filtration/filling, this reduces to ≈140 ± 20 g purified rhPBGD, based on an overall recovery of 35 ± 5% (f = 1 × 0.55 × 0.9 × 0.9 × 0.85 × 0.93 ≈ 0.35 for 1 × steps (i) to (v), respectively). Thus, allowance is made for improvement of the Blue Sepharose step (i) from about 35% to 55% and the final TFF and associated steps (iv) + (v) from ≈70% to ≈80% (cf. footnotes in Table 3; f ≈ 1 × 0.35 × 0.9 × 0.9 × 0.7).
If a more concentrated solution is desired (e.g. 8 ± 2 mg rhPBGD/mL) then total end volume range would be adjusted accordingly.

TABLE 7

Efficiency of process steps (2 × Blue Sepharose) - Test run:

| | | | % Yield of rhPBGD: | | | | | |
|---|---|---|---|---|---|---|---|---|
| | | Amount | Relative to start | | | Relative to prior step | | |
| Process Step | | (g) | Mean | | | Mean | | |
| Crude Load | | | | | | | | |
| Total protein | (i) 71 Kg × 8.8 plus | 1324 g | | | | | | |
| | (ii) 79.5 Kg × 8.8 mg/mL | | | | | | | |
| (HPLC purity) | ≥ 40% | 397 g | 100 | | | 100 | | |
| rhPBGD (as 30 ± 10% of total) | 397 ± 132 g | | | 100 | | | 100 | |
| rhPBGD[1] | 150.5 Kg × 3.475 mg/mL | 523 g | 100 | | | 100 | | |
| Blue Sepharose (2 ×) | (i) + (ii) | 203 g | 51% | 39% | 45% | 51% | 39% | 45% |
| | 181.3 Kg × 1.12 mg/mL | | | | | | | |
| (HPLC purity) | >91% | | | | | | | |
| DEAE Sepharose | 120 Kg × 1.35 mg/mL | 162 g | 41% | 31% | 36% | 80% | 80% | 80% |
| (HPLC purity) | >99% | | | | | | | |
| Ceramic Hydroxyapatite | 100 Kg × 1.48 mg/mL | 148 g | 37% | 28% | 32% | 91% | 91% | 91% |
| (HPLC purity) | >99% | | | | | | | |
| Diafiltration (TFF) | "11.6 L" × 11.2 mg/mL | 130 g | 33% | 25% | 29% | 88% | 88% | 88% |
| (HPLC purity) | >99% | | | | | | | |
| 0.2 μm final filtration/filling | 14.2 L × 8.3 mg/mL | 118 g | 30% | 23% | 26% | 91% | 91% | 91% |
| (HPLC purity) | >99% | | | | | | | |

Notes
[1] HPLC method; Relative to reference rhPBGD determined by BCA protein method.

TABLE 8

Efficiency of process steps (2 × Blue Sepharose) - DEAE and CHT parameters optimised compared to HB001E3:

| Process Step | Amount (g) | | % Yield of rhPBGD: | | | | | |
|---|---|---|---|---|---|---|---|---|
| | | | Relative to start | | | Relative to prior step | | |
| | | | | | Mean | | | Mean |
| Crude Load | | | | | | | | |
| Total protein | (i) + (ii) | 1400 g | | | | | | |
| (HPLC purity) | 160 Kg × 8.8 mg/mL ≧40% | 420 g | 100 | | | 100 | | |
| rhPBGD (as 30 ± 10% of total) | 420 ± 140 g | | | 100 | | | 100 | |
| rhPBGD[1] | 160 Kg × 3.38 mg/mL | 541 g | | 100 | | | 100 | |
| Blue Sepharose (2 ×) (HPLC purity) | (i) + (ii) 192 Kg × 1.04 mg/mL >91% | 200 g | 48% | 37% | 42% | 48% | 37% | 42% |
| DEAE Sepharose (HPLC purity) | 90 Kg × 2.09 mg/mL >99% | 188 g | 45% | 35% | 40% | 94% | 94% | 94% |
| Ceramic Hydroxyapatite (HPLC purity) | 90.2 Kg × 2.06 mg/mL >99% | 186 g | 44% | 34% | 39% | 99% | 99% | 99% |
| Diafiltration (TFF) (HPLC purity) | 16.5 Kg × 9.67 mg/mL >99% | 160 g | 38% | 30% | 34% | 86% | 86% | 86% |
| 0.2 μm final filtration/filling (HPLC purity) | 17.5 L × 8.43 mg/mL >99% | 148 g | 35% | 27% | 31% | 93% | 93% | 93% |

Notes
[1]HPLC method; Relative to reference rhPBGD determined by BCA protein method.

5. Materials and Methods

| Equipment/systems list | Specification |
|---|---|
| WFI system | KemiTerm, ME75 |
| Nitrogen system:, | Strandmøllen |
| CIP/SIP system, | Danprocess |
| LPLC system, | DanProcess |
| LPLC steel column 40 cm diam., | DanProcess |
| BPG LPLC glass column 45 cm diam. | Pharmacia |
| BPG LPLC glass column 45 cm diam. | Pharmacia |
| Process Tanks: T01, T02 (Product Tanks), | custom made |
| T03, T10 (Buffer Tanks), | custom made |
| T30 (Buffer preparation tank) | custom made |
| In-line Mixer, | |
| Ultrafiltration system/in-line strainer 100 μm, | Millipore |
| LAF bench HB2470, | Heto-Holten A/S Allerød |
| Balance, | Mettler Toledo |
| pH meter, | Knick, Model 911 |
| Conductometer, | Orion and VTV |
| Osmometer, | Gono Tec, Osmomat 030 |
| Spectrophotometer | |
| Analytical HPLC, | HP |
| Dry Sterilising Oven, | Heraeus UT 6120 |

TABLE 9

| Raw materials list | | | |
|---|---|---|---|
| Product name | $M_r$ | Product name | $M_r$ |
| Crude rhPBGD (BioGaia Fermentation AB) | (37.627) | Mannitol | 182.171 |
| $K_2HPO_4$ | 174.18 | Purified water including WFI | (18) |
| $KH_2PO_4$ | 136.09 | NaOH, 28% | 40 (9.66 M) |
| KCL | 74.55 | $H_3PO_4$, 85% | (14.70 M) |
| $Na_2HPO_4 \cdot 2H_2O$ | 177.99 | EtOH, 96% | 46.068 |
| Glycine | 75.068 | Nalgene PETG flasks (1 L) | |
| Nitrogen | 14 | Emflon II 5" Luftfilter | |
| PolyCap™ 150 PES Capsule | | MembraCart PES Ph. 0.2 μm 10" | |
| Biomax 10 V 0.5 m² filter | | PreCart PP II Pharma 1.0 μm 10" | |
| Blue Sepharose 6FF | | PreCart PP II 3.0 μm 10" | |
| DEAE Sepharose FF | | PreCart PP II Pharma 5.0 μm 10" | |
| CHT Ceramic Hydroxyapatite Type I, 40 μm | | | |

Method E 001:2

Enzymatic assay where the enzyme containing fraction is incubated with the substrate porphobilinogen (PBG) for 5 minutes at 37° C. at pH 8.2. The reaction is terminated by addition of HCl. PBGD will convert 4 molecules of PBG to the product preuroporphyrinogen (linear tetramer). Preuroporphyrinogen is then chemically oxidized with benzoquinone to form uroporphyrinogen, which could be measured spectrophotometrically at 405 nm.

Method P 001:2

Protein concentration is determined by a commercially available method from Pierce (BCA method) that utilizes the principle of the reduction of $Cu^{2+}$ to $Cu^+$ by protein in alkaline medium (Biuret reaction). The $Cu^+$ ions are thenreacted with a reagent containing bicinchoninic acid resulting in a highly sensitive and selective colorimetric detection at 562 nm. Results are correlated against a BSA standard curve. Absorbance interval is 0.1–1.0

Method R 001:2

Measurement of HPLC purity is determined as the area under curve for the specific rhPBGD peak in relation to total integrated area of all detected peaks. The sample is injected and analyzed on a Zorbax-CN column (start 80% A and 20% B buffer). The buffers used are: Buffer A: H2O+0.1% TFA; Buffer B: Acetonitrile+0.1% TFA. Proteins are eluted with an increasing concentration of B buffer (linear gradient from 20 up to 90% B) and detected with UV absorption at 220 nm.

Method E005:1

The method is an ELISA method where ELISA plates are coated with ECP antibodies. The ECP's in samples and standards added to the plate will bind to the coating antibodies and are detected via biotinylated ECP antibodies. A streptavidin-horseradish peroxidase (HRP) conjugate is added which converts the substrate tetramethylbenzidine (TMB) to a blue product. The reaction is stopped upon acidification that converts the blue product into a yellow product that could be measured at 450 nm.

Method D002:0.1

Residual DNA is quantified using the Threshold System in which the heat-denatured DNA is labeled with a streptavidin-containing reagent. The DNA-streptavidin complexes are captured on a biotinylated nitrocellulose membrane where the antibody-conjugated urease activity is detected by a change in the surface potential. The rate of change in surface potential is correlated to the amount of DNA in the sample. The concentration of DNA in the sample can be quantified by comparing to a standard curve with known amount of DNA.

6. Conclusion

Three large scale manufacturing purification processes which allow the isolation of highly purified rhPBGD from 100–300 L of crude rhPBGD extract are described:

Process 1.

Starting from 100–300 L of crude rhPBGD extract, or 1–1.5 Kg total protein this process gives an overall process yield of about 100 g (96 g actual) of purified rhPBGD at >90% HPLC purity (>98% actual). The analytical quality specifications were met (Table 4). The overall recovery of rhPBGD was about 22%.

Process 2.

Process 2 is an extension of Process 1. A Ceramic Hydroxyapatite (CHT) chromatography step has been added. The addition of this step resulted in a 100-fold reduction of E. coli proteins (ECP), high HPLC purity was maintained (>99%), and the analytical quality specifications required for clinical studies were achieved (Table 5). The overall yield was about 20%.

Process 3.

Upgraded version of process 2 where the main improvement is related to the relatively lower load on the blue sepharose column resulting in significantly higher yields (compare table 8 with table 3).

EXAMPLE 2

PBGD Porphobilinogen Activity Assay

Below is a detained description of the PBGD porphobilinogen activity assay, used throuogout this study to determine the activity of rhPBGD.

Materials and Equipment

Spectrophotometer HP 8453 from Hewlett Packard or equivalent

Cuvettes 1 or 3 ml (glass or plastic) with 1 cm path-length suitable for 405 nm

Chemicals and Reagents

Porphobilinogen (no.P1134, Sigma)

BSA—Bovine Serum Albumin Frac. V (no. 1.12018, Merck)

p-Benzoquinone (no.B1266, Sigma)

Sodium metabisulfite (no.S9000, Sigma)

Methanol p.a (Merck)

All other solvents and chemicals were of pro analysi (p.a.) quality (Merck)

a. Assay buffer: 50 mM Tris-HCl pH 8.2+1 mg/ml BSA included. Store cold for maximum 2 weeks. Sterile-filtered (0.22 μm) stock solution of 1M Tris-HCl pH 8.2 could be stored cold for 6 months and diluted 1:20 before usage.
b. PBG solution: 8 mM PBG in 50 mM Tris-HCl pH 8.2. Prepare fresh or store frozen (−20° C.) in aliquots for a maximum of 4 weeks.
c. Benzoquinone solution: Prepare fresh by dissolving 0.1% (w/v) benzoquinone in methanol.
d. Saturated sodium metabisulfite solution: mix 1.5 g sodium metabisulfite with 2 ml water. Prepare fresh.
e. 5 M HCl
f. 1 M HCl Method Sample Preparation Prepare the extract by spinning down cell debris and particles and filter supernatant through a 0.45 μm filter. PBGD pools from the purification process and rhPBGD final product could be measured directly if they appear clear and non-turbid. Otherwise, filter through a 0.45 μm filter.

Determine the protein concentration of the samples using the BCA Protein Assay Reagent kit as described in Heme-Biotech Procedure 006.

Method Procedure

Aim to achieve a final absorbance between 0.3 and 0.8 by adding 1 to 50 μl of sample. Linearity could be a problem at absorbances above 0.8 and should therefore be avoided.

a. Mix an aliquot of sample (1–50 μl) and add assay buffer to a total volume of 100 μl. Pre-incubate for 2 minutes at 37° C. For blank sample, use 100 μl of assay buffer.
b. Initiate reaction by adding 50 μl of pre-warmed (37° C.) 8 mM PBG solution. Incubate at 37° C. for 5 minutes.
c. Terminate reaction by adding 65 μl of 5 M HCl followed by 25 μl benzoquinone solution in order to oxidize the porphyrinogenes to porphyrines. Incubate for 20 minutes in the dark and on ice.
d. Add 50 μl of saturated sodium metabisulfite solution to decolorize any remaining benzoquinone.

e. Add 2.60 ml of 1 M HCl solution in order to dilute the sample 10 times and centrifuge at 3.000 g for 10 minutes to remove particles and precipitated protein.

f. Measure the absorbance at 405 nm. Calculate the delta absorbance (ΔA) by subtracting the absorbance value of the blank from the measured absorbance of each of the samples. The molar extinction coefficient ($\epsilon M$) for the product uroporphyrin is $5.48 \times 10^5$ M−1 cm−1.

g. As a positive control (system suitability test), measure enzyme activity of the rhPBGD standard or rhPBGD-His standard. Adapt volumes and so that the final absorbance will be within the range 0.3–0.8. Activity of the standard extract or rhPBGD standard should, be within the range as the previous measurement (+/−20%). A slight decrease in activity over time is however expected for the rhPBGD and rhPBGD-His standard. Store activity values of standards and plot activity trends over time.

Calculations

Definition.

One Unit (1 U) of enzyme activity is defined as the amount of porphobilinogen deaminase needed to consume 1 µmole of porphobilinogen per hour.

In order to calculate the enzyme activity in µmole PBG consumed/hour×ml (=Units/ml) the following equation should be used:

$$(\Delta A \times 4 \times 12 \times 10^6 \times V_{tot(ml)})/(V_{sample(\mu l)} \times \epsilon_M) = X \text{ µmole}/(\text{hour} \times ml) = \text{Units/ml} \quad (1)$$

where:

ΔA=absorbance of sample−absorbance of blank

4=4 moles PBG consumed per mole uroporphyrin produced in the assay

12=if measuring 5 minutes, multiply by 12 to get 1 hour (60 min)

$10^6$=converting M to µM $V_{tot(ml)}$=total reaction volume in ml (in this case 2.89 ml)

$V_{sample(\mu l)}$=added sample volume in µl $\epsilon_M$=the molar extinction coefficient for the product uroporphyrin, which in this case is $5.48 \; 10^5$ M$^{-1}$ cm$^{-1}$ Equation 1 could more simplified be written as:

$$(\Delta A \times 1.3872 \times 10^8)/(V_{sample(\mu l)} \times 5.48 \times 10^5) = X \text{ µmole}/(\text{hour} \times ml)(=\text{Units/ml}) \quad (1)$$

To calculate the specific activity in µmole PBG consumed/hour×mg (=Units/mg) divide equation 1 with the protein concentration of the sample:

$$Eq. \; 1/\text{Protein conc. (mg/ml)} = Y \; \text{µmole}/(\text{hour} \times mg) = \text{Units/mg} \quad (2)$$

Note: Other definitions used in litterature is:

nanomoles uroporphyrinogen produced per mg PBGD per hour

Conversion factor: 1000 (nmol/µmol)/4 moles PBG/mole uroporphyrinogen=250

(Ref: Shoolingin-Jordan P. M. et al. 1997, Methods in Enzymology, 281:317–327).

EXAMPLE 3

Comparison of the Large-Scale Procedure of WO 01/07065 with the Procedures in Example 1

Background and Experimental Details

The 100 ml intermediate scale process described in example 7 of WO01/07065 was scaled up to 10–12 L gels for the production process and run essentially as described but with a few changes that refers to changes from intermediate scale and reflect normal scale-up adaption and therefore changes are considered to be non-essential for the overall comparasion, but essential for the larger scale.

Results

A summary of the results obtained with an upscaled version of the process described in example 7 of WO01/07065 is showed in tables 10 and 11 below

TABLE 10

Process 1. Production runs 2 and 3 - Summary of Yields

| Production Runs | | batch 1 Analytical results* | | Batch 2 Analytical results* |
|---|---|---|---|---|
| Process Steps | (i) | Total protein | (i) | Total protein |
|  | (ii) | rhPBGD content | (ii) | rhPBGD content |
|  | (iii) | Yield (%) | (iii) | Yield (%) |
| Crude rhPBGD | (i) | 550 g | (i) | 265 g |
| Load | (ii) | 186.5 g | (ii) | 116 g |
|  | (iii) | 100% | (iii) | 100% |
| Phenyl Sepharose | (i) | 283 g | (i) | 165 g |
|  | (ii) | 154 g | (ii) | 87 g |
|  | (iii) | 82.3% | (iii) | 75% |
| DEAE Sepharose pool | (i) | 20.8 g | (i) | 40 g |
|  | (ii) | 10 g | (ii) | 33 g |
|  | (iii) | 5% | (iii) | 28% |
| Blue sepharose pool | (i) | 9.3 g | (i) | 18.5 g |
|  | (ii) | 8.8 g | (ii) | 16.6 g |
|  | (iii) | 4.7% | (iii) | 14% |
| Sterile filled bulk drug substance | (i) | 6.9 g | (i) | 12.7 g |
|  | (ii) | 6.7 g | (ii) | 12.3 g |
|  | (iii) | 3.6% | (iii) | 10.6% |

*Data presented above are based on the analytical methods described in example 1.

TABLE 11

Analytical summary of bulk drug substance 26P5-2STF and 26P5-3STF, respectively

| Batch | Amount (g) | Conc. (mg/ml) | Volume (L) | Purity (%) | Spec. activity (U/mg) | ECP level (i g/mg) | Endo-toxin (U/mg) | residual DNA (pg/mg) |
|---|---|---|---|---|---|---|---|---|
| 1 | 6.9 | 6.6 | 1.05 | 96.7 | 12.5 | 2.5 | Approved (<5 IU/mg) | Approved |
| 2 | 12.7 | 8.3 | 1.53 | 97.0 | 12.3 | 5.0 | Approved (<5 IU/mg) | Approved |

Comments and Conclusions

According to the analytical data presented in Table 11, it is possible to produce purified rhPBGD of a purity sufficient for toxicology testing using the above described method. However, several technical problems were noticed when running the process in the large scale, making this process not useful for continuous production. The main reasons for that are listed below:

1. Precipitation problems were noticed during the first HIC step
2. Low yield were seen from the DEAE chromatography step, where most of the protein was lost.
3. The DEAE had to be re-packed at approximately 50% of the ordinary volume and with reduced load (25–35% in 3 to 4 repetitive runs) from the pool from the HIC step in order to function without too many problems.
4. The overall yield from the process was very low (3.6 and 10.6% respectively). The quality of the final bulk drug substance was however approved.

Therefore, it was decided to rebuild the purification process and and invent a completely new purification process presented in example 1. With the new process it is possible to obtain 31% yield of a >99% pure rhPBGD (process 3) that is suitable for clinical purposes.

EXAMPLE 4

Results from Clinical Trials

The clinical studies of the product of the present invention are carried out in accordance with the HemeBiotech trial protocol dated 30 Aug. 2001, Amendment 1 dated 15 Nov. 2001, Amendment 2 dated 21 Jan. 2002, Amendment 3 dated 31 Jan. 2002 and Amendment 4 dated 11 Mar. 2002. The trial protocol including amendments is approved by the Swedish Medical Products Agency (MPA) and the Ethics Committee of Stockholm County.

Safety, tolerability and the pharmacokinetics of a single and repeated dose of i.v. rhPBGD have been studied. In addition, the biochemical efficacy have been investigated by measuring the change in plasma concentration of PBG over time for both single and repeated dose(s) of rhPBGD.

Methodology

The study consists of 2 separate parts.

Part A is a dose escalating, open label rhPBGD single dose study

Part B is a double blind, randomized, parallel group, placebo controlled repeated dose, pharmacokinetic, efficacy (biochemical), safety and tolerability trial.

Two dose groups (0.5 mg/kg and 1.0 mg/kg) are included in the present analysis.

Number of Patients

In this preliminary analysis a total of 19 subjects are included. Six subjects have been started on trial drug (part A) and a total of 19 subjects have been randomised on trial product or placebo (part B).

Diagnosis and Main Criteria for Inclusion

Male and/or female subjects aged 18–65 years, who are considered healthy except for manifest AIP defined as urinary excretion of PBG >4.8 mmol/mol creatinine (i.e. 4 times above upper reference level) and with confirmed mutation for diagnosis and no clinical symptoms of acute AIP within the last 6 months, as determined by the investigator and the subject.

Furthermore, non-AIP (healthy male) subjects are in addition selected to take part in the repeated dose trial in part B.

Test product:rhPBGD for i.v. injection, produced according to the procedure described in example 1. Only batches Clin 2, Clin 3 and Clin 4 were used for clinical testing. The analytical data for the batches can be found in table 5, example 1.

Total Daily Dose: 0.5 mg/kg and 1.0 mg/kg

Mode of administration: Intravenous, bolus injection.

Duration of Treatment

The total doses are the same in part A and part B.

Part A: Single dose.

Part B: Repeated dose (Twice daily, BID) for 4 days. The daily dose in part B is split in two portions: 0.25 mg/kg and 0.5 mg/kg, given twice daily with 12 hours intervals.

Reference Therapy

Placebo is intravenous, bolus injection(s) of formulation buffer (Sodium $HPO_4$ (3.16 mM), Sodium $H_2PO_4$ (0.51 mM), Glycine (27 mM), Mannitol (222 mM), Water for injection (WFI) qs.; pH 8.0±0.5)

Criteria for Evaluation

Biochemical Efficacy

To study the biochemical efficacy based on the change in plasma concentration of PBG over time, the relative reduction in plasma PBG concentration at time t from baseline (time=0) was calculated as:

$$R_t = 100 \times (1 - (PBG_t/PBG_0)) \text{ for all time points.}$$

Pharmacokinetics

The following pharmacokenetic parameters are presented:
1) The maximum rhPBGD plasma concentration ($C_{max}$)
2) Terminal half-life ($t_{1/2}$)

Safety

Occurrence of clinical Adverse Event(s).

Occurrence of significant laboratory results (hematology, clinical chemistry and urinalysis) outside normal reference range and judged clinically relevant by the investigator.

Physical examination, vital signs and ECG.

Assessment of antibody formation to rhPBGD.

Summary of Results

As the total daily dose in part B was split in two, the 12 hours results in part B are based on half of the dose per injection compared to part A.

Efficacy results

Biochemical Efficacy,

Descriptive statistics are presented for part A day 1 ($R_{max}$, treatments: dose groups 0.5 mg/kg and 1.0 mg/kg) and for part B day 1 and day 4 ($R_{max}$, treatments: placebo, dose groups 0.5 g/kg and 1.0 mg/kg) in table 8 below.

TABLE 12

Biochemical Efficacy summary Statistics, the maximum relative plasma PBG reduction ($R_{max}$)

Part A Day 1

| | Rmax (%) | |
|---|---|---|
| | 0.5 mg/kg | 1.0 mg/kg |
| N | 3 | 3 |
| Mean | 99.89 | 100 |
| Geometric mean | 99.89 | 100 |

Part B Day 1

| | rhPBGD | |  |
|---|---|---|---|
| | Placebo | 0.5 mg/kg | 1.0 mg/kg |
| | | Rmax (%) | |
| | AIP | AIP | AIP |
| N | 2 | 2 | 4 |
| Mean | 40.871 | 97.925 | 100 |
| Geometric mean | 39.087 | 97.903 | 100 |

Part B Day 4

| | rhPBGD | | |
|---|---|---|---|
| | Placebo | 0.5 mg/kg | 1.0 mg/kg |
| | | Rmax (%) | |
| | AIP | AIP | AIP |
| N | 2 | 2 | 4 |
| Mean | 47.726 | 100 | 100 |
| Geometric mean | 46.518 | 100 | 100 |

$R_t = 100 * (1 - (PBG_t/PBG_0))$ (%).
N = number of individuals.
AIP = Acute Intermittent Porphyria patient.

Figure 2:
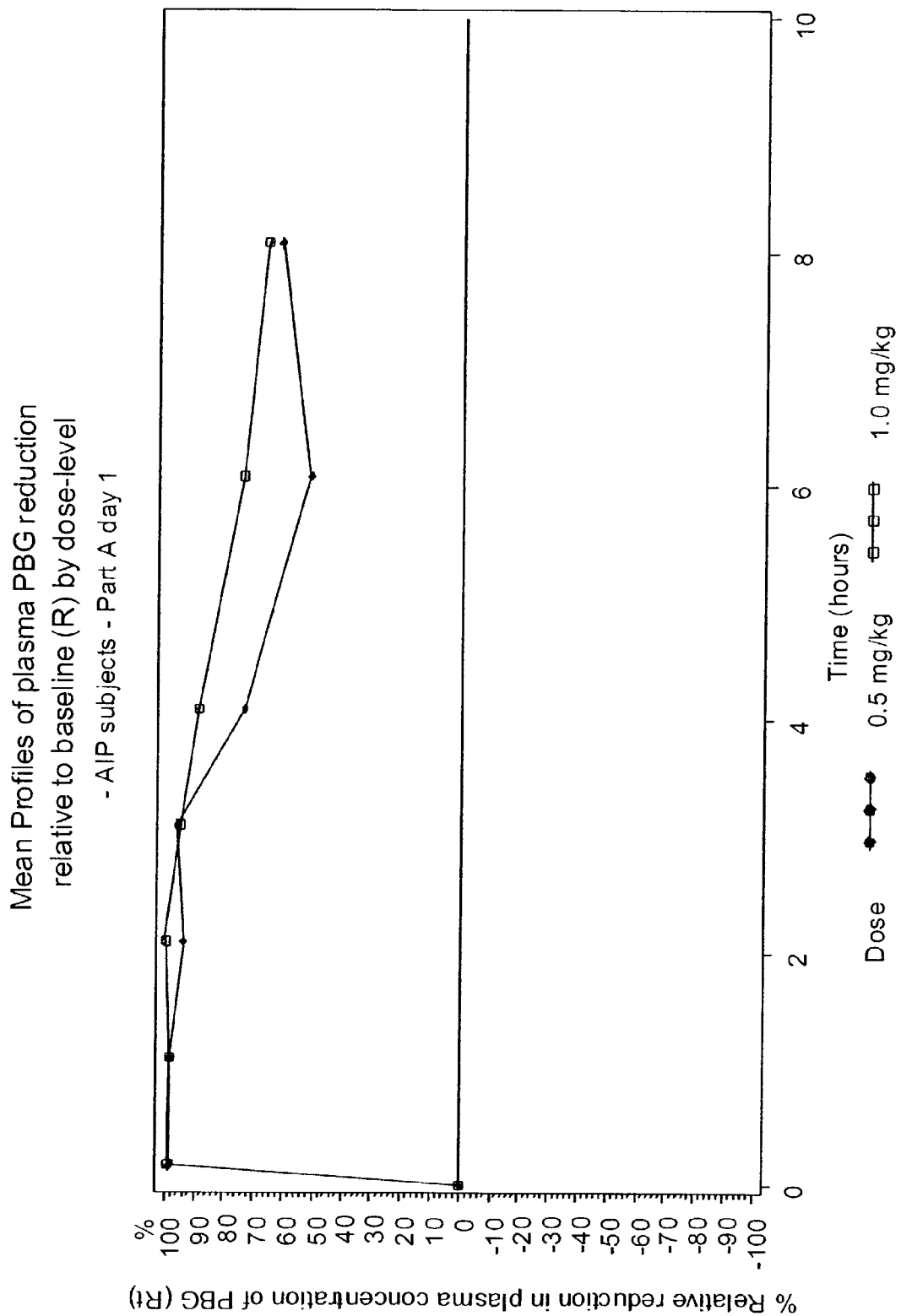
Figure 3:
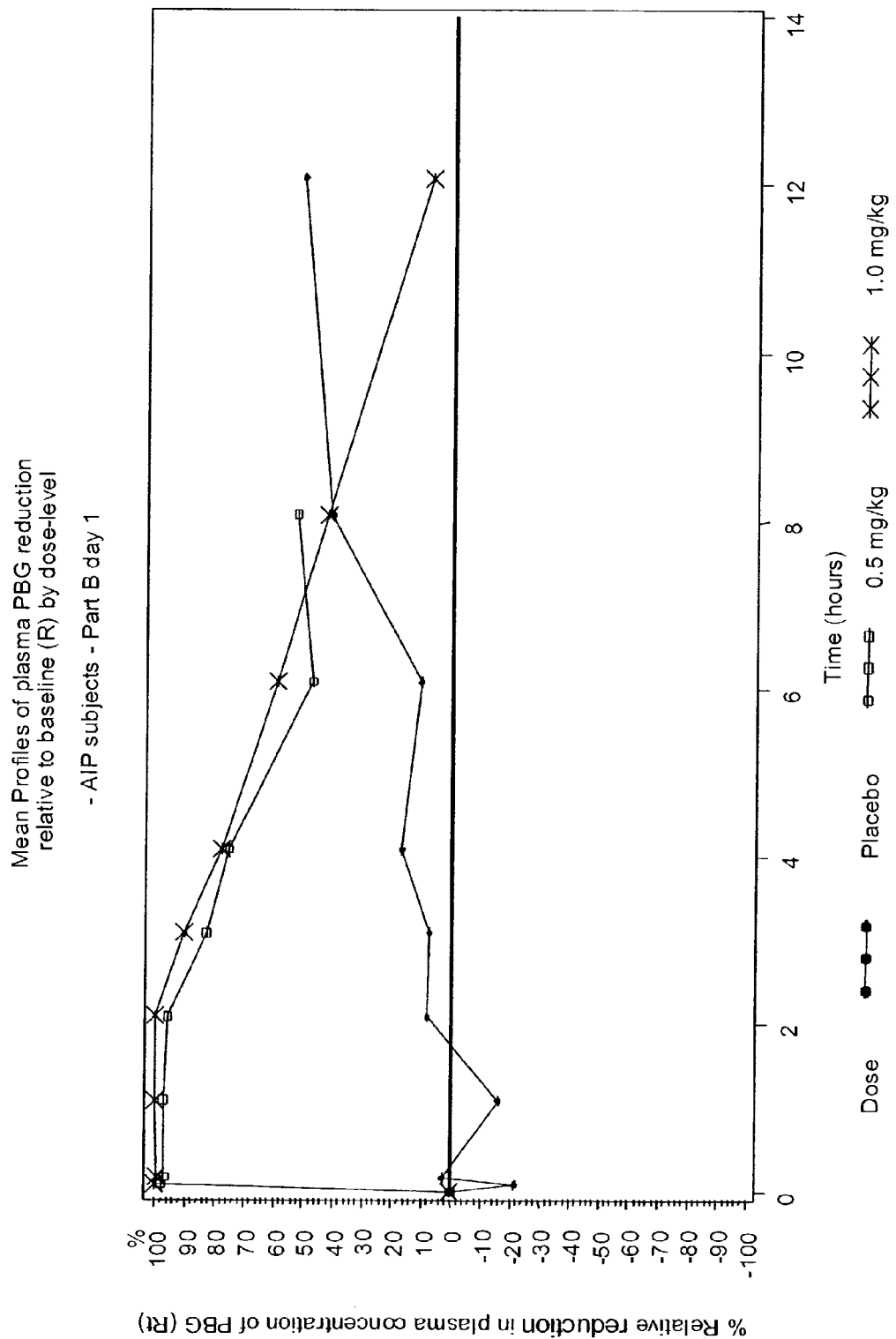
Figure 4:
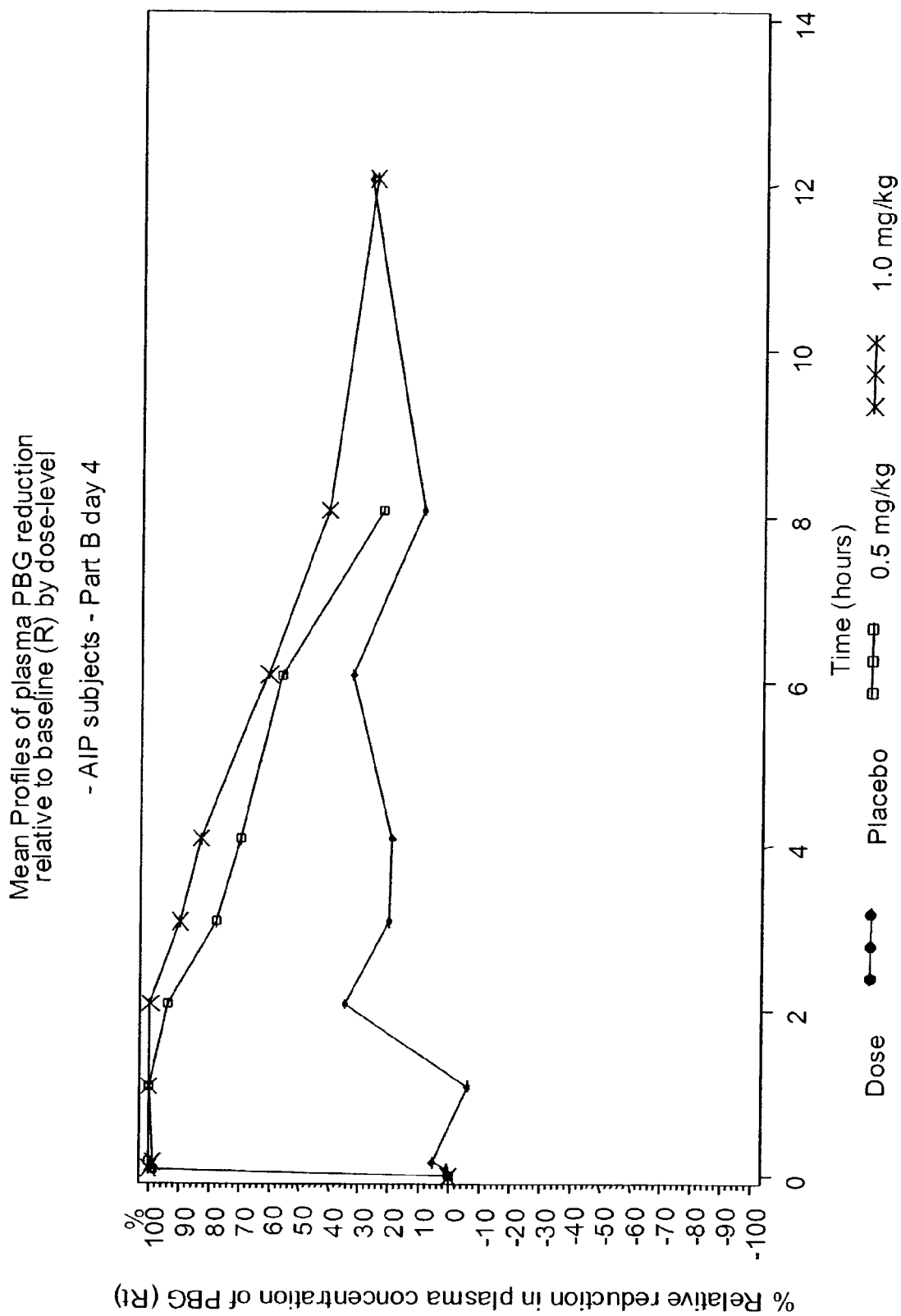

Evidence is presented (Table 12) that the rhPBGD produced as described in example 1 is efficient in reducing the PBG concentrations in plasma of patients. Further evidence is presented in FIGS. 2, 3 and 4.

Part A

The result from study part A (FIG. 2) shows that for dose groups 0.5 mg/kg and 1.0 mg/kg the mean reduction of plasma PBG is close to 100% during the first 3 hours. Between 3–8 hours the reduction is slightly lower for dose group 0.5 mg/kg compared to dose group 1.0 mg/kg indicateting a dose effect of rhPBGD on the PBG.

Part B Day 1

For dose groups 0.5 mg/kg (given as two 0.25 mg/kg doses with 12 hours intervals) and 1.0 mg/kg (given as two 0.5 mg/kg doses with 12 hours intervals), the mean reduction of plasma PBG is close to 100% during the first 2 hours. Between 2–6 hours the reduction is slightly lower for dose group 0.5 mg/kg compared to dose group 1.0 mg/kg and at 8 hours the reduction is slightly higher for dose group 0.5 mg/kg than for 1.0 mg/kg. During the first 8 hours the reduction of plasma PBG for placebo is on a lower level than for dose groups 0.5 mg/kg and 1.0 mg/kg. See FIG. 3. Taken together these results indicate a dose effect of rhPBGD on the PBG on the size and duration of the relative PBG reduction from baseline.

Part B Day 4

During the first hour, the mean reduction of plasma PBG relative to baseline is close to 100% for dose groups 0.5 mg/kg (2×0.25 mg/kg) and 1.0 mg/kg (2×0.5 mg/kg). Thereafter, the reduction is on a lower level for dose group 0.5 mg/kg compared to dose group 1.0 mg/kg. For placebo compared to dose groups 0.5 mg/kg and 1.0 mg/kg, the reduction is on a lower level during the first 8 hours (see FIG. 4). As is the case for day 1, dose response effect was observed. Also as is the case for day 1, the effect of rhPBGD is clearly different from the effect of placebo, see also Table 12.

Pharmacokinetics

Selected descriptive statistics were presented for pharmacokinetic endpoints (see Table 13 below), i.e. no formal statistical analyses were performed.

There is no indication of any accumulation of the drug.

For part A (see Table 13) dose group 0.5 mg/kg, the harmonic mean of $t_{1/2}$ of rhPBGD is 98 min. For dose group 1.0 mg/kg the harmonic mean is 77 min. Since only the three final valid concentrations were used for determination of half-lives, there is a high variability on these determinations ranging from ½ hour to 4½ hours. The harmonic mean of all valid determinations is about 1¼ hour.

A similar trend is seen for the $t_{1/2}$ obtained in part B of the study. However, results obtained both on day 1 and on day 4 indicate a lower harmonic mean in dose group 0.5 mg/kg than in dose group 1.0 mg/kg.

Since the half-life estimates are based on the three last valid and rather low concentrations only, they are highly variable ranging from half an hour to four and a half hour. However, the harmonic mean of all valid estimates is about one and a quarter of an hour.

TABLE 13

Summary Statistics of rhPBGD Pharmacokinetic Endpoints

| | rhPBGD | |
|---|---|---|
| Part A Day 1 | 0.5 mg/kg | 1.0 mg/kg |
| Cmax (ng/ml) | | |
| N | 3 | 3 |
| Geometric mean | 23690 | 4537 |
| t½ (min) | | |
| N | 3 | 3 |
| Harmonic Mean | 98 | 77 |

| | | rhPBGD | | | | |
|---|---|---|---|---|---|---|
| | Placebo | 0.5 mg/kg | | 1.0 mg/kg | | |
| Part B Day 1 | All | All | AIP | All | AIP | |
| Cmax (ng/ml) | | | | | | |
| N | | 6 | 2 | 8 | 4 | |
| Geometric mean | 9994 | 15822 | 21406 | 14252 | | |
| t½ (min) | | | | | | |
| N | | 6 | 2 | 8 | 4 | |
| Harmonic Mean | | 59 | 46 | 76 | 101 | |

| | | | rhPBGD | | | |
|---|---|---|---|---|---|---|
| | Placebo | | 0.5 mg/kg | | 1.0 mg/kg | |
| Part B Day 4 | All | AIP | All | AIP | All | AIP |
| Cmax (ng/ml) | | | | | | |
| N | 1 | | 7 | 3 | 8 | 4 |
| Geometric mean | 70 | | 10788 | 16231 | 18111 | 13537 |
| t½ (min) | | | | | | |
| N | | | 7 | 3 | 8 | 4 |
| Harmonic Mean | | | 53 | 64 | 87 | 72 |

Cmax = The Maximum rhPBGD plasma concentration.
t½ = terminal half-life of rhPBGD.
N = number of patients.

Figure 5:
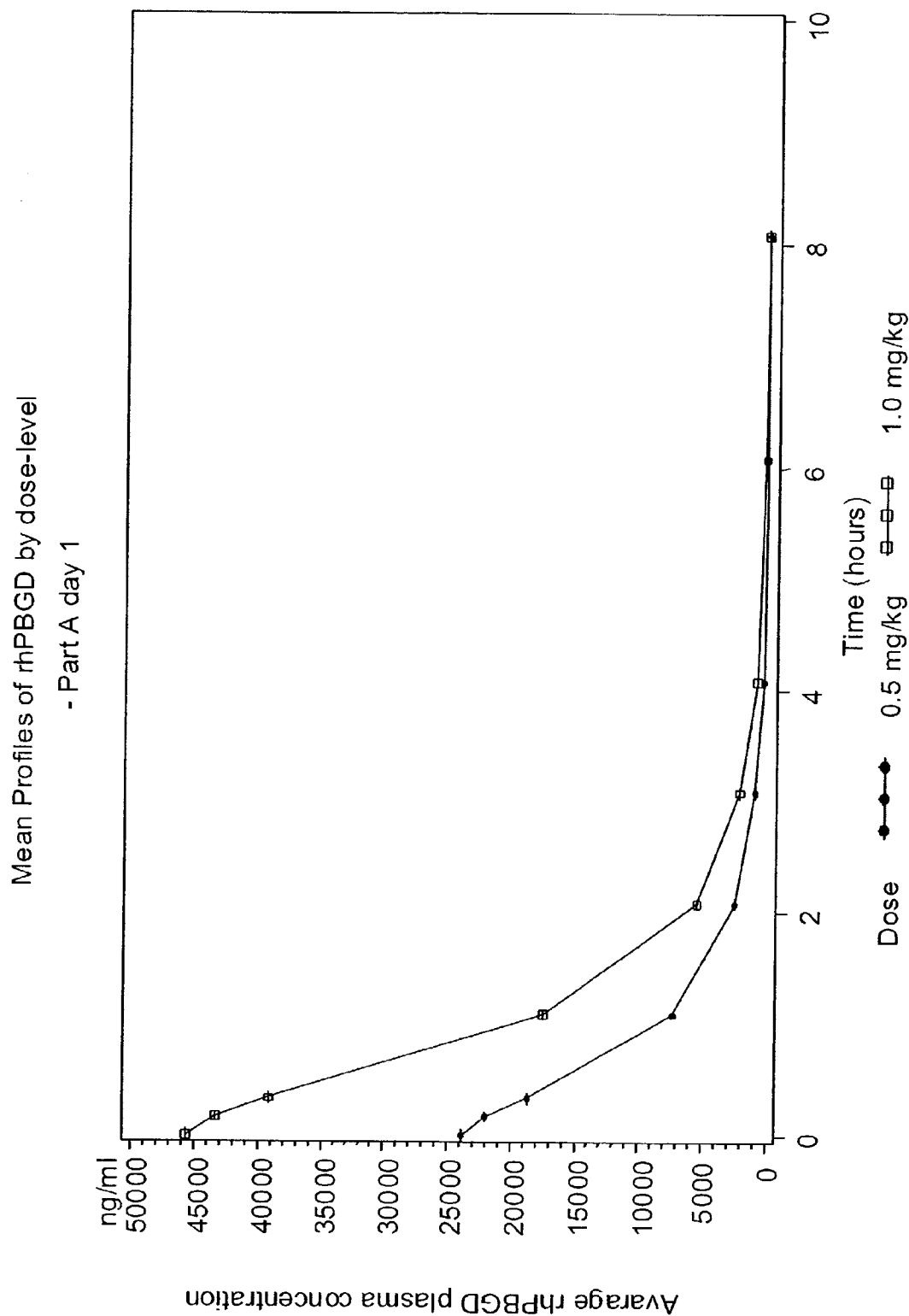
Figure 6:
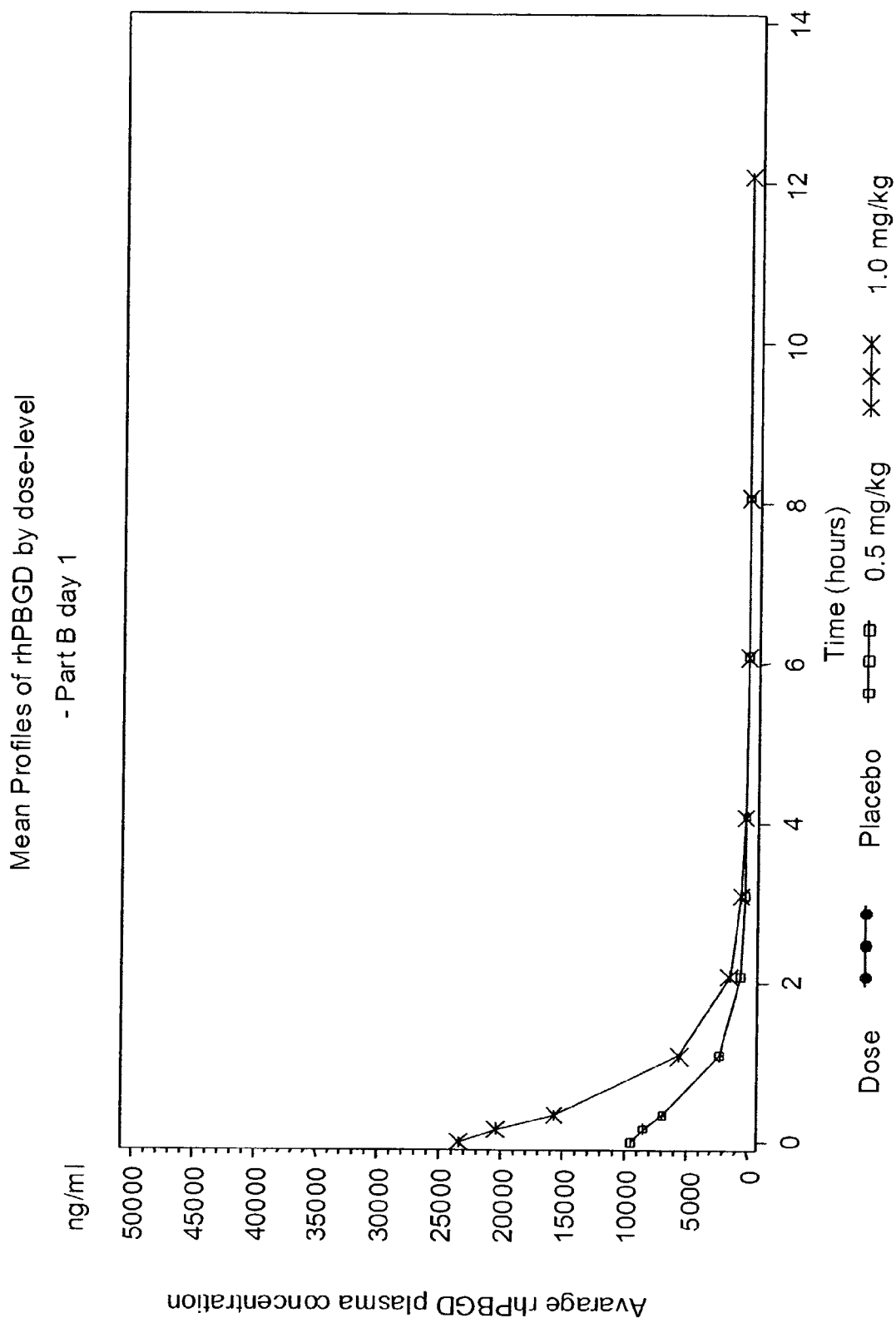
Figure 7:
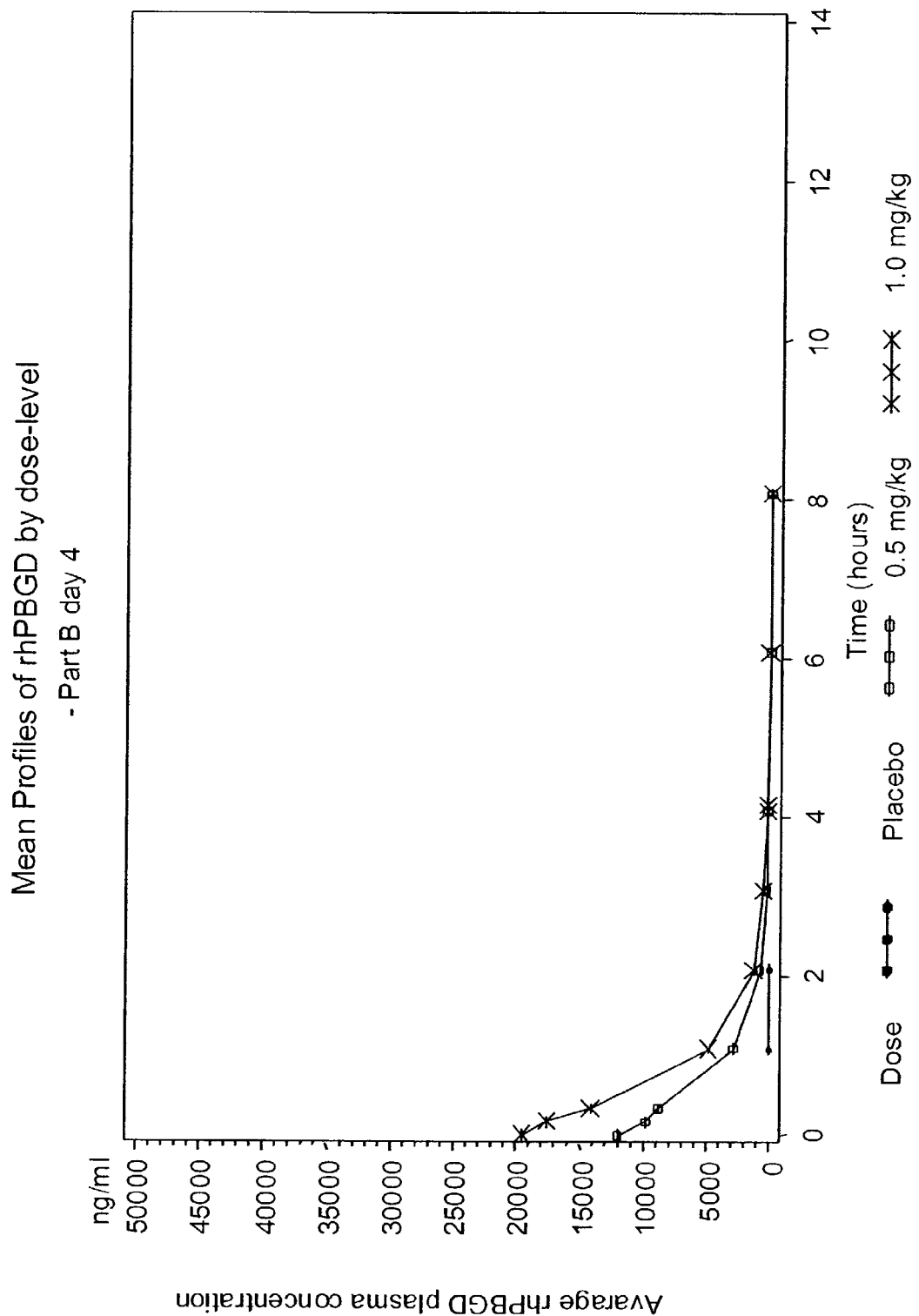

From FIG. 5 it appears that the average rhPBGD plasma concentration is very close to zero already 4 hours after drug administration. The results from part B of the study show that the rhPBGD is removed even faster from the plasma when the dose is split in two. As shown in FIGS. 6 and 7, the average rhPBGD plasma concentration is very close to zero 3 hours after drug administration.

Safety Results

In total 9 subjects (6 AIP and 3 non-AIP male subjects) out of 19 reported adverse events. None were reported as Serious Adverse Events and all were reported as mild to moderate in intensity. None of the adverse events were classified by the investigator to be related to trial drug.

An increase of IgG antibodies to rhPBGD was observed in several subjects. No clinical allergic reactions have been observed.

For the physical examination, ECG monitoring, vital signs and laboratory data contains no clinical observations of concern.

Conclusions

No overall safety concern is raised from the data representing this sub-population.

rhPBGD is efficient in reducing the PBG concentrations in plasma instantly.

maximum rhPBGD concentration is reached immediately after injection.

rhPBGD is removed relatively fast from the body. The terminal half-life of rhPBGD is about ½–4½ hour.

There is no indication of any accumulation of the drug.

The invention claimed is:

1. A process for purification of recombinant human porphobilinogen deaminase (rhPBGD) on an industrial scale from a rhPBGD containing extract obtained from a fermentation of a recombinant cell capable of expressing rhPBGD, characterized by following steps:

(i): prior to any other chromatography column purification step, loading the rhPBGD containing extract on an equilibrated Cibacron Blue 3G sepharose affinity chromatography column having a column volume of at least 5 L and, after adequate washing step(s), eluting a sample comprising rhPBGD;

(ii) : loading the eluent of step (i) on an equilibrated chromatography column having a column volume of at least 5 L and, after adequate washing step(s), eluting a sample comprising rhPBGD;

(iii) : performing one or more further chromatography column step(s) wherein the chromatography column is a column relying on a different principle than an affinity chromatography column and also relying on a different principle than the column used in step (ii), eluting a fraction comprising rhPBGD, and collecting said fraction, where said rhPBGD has porphobilinogen deaminase activity and is bound by Cibacron Blue 3G.

2. The process of claim 1, wherein the column volume of the affinity chromatography column of step (i) is at least 10 L.

3. The process of claim 1, wherein the affinity chromatography column of step (i) is a column using a triazine coupling as ligand coupling method.

4. The process of claim 1, wherein chromatography column of step (ii) is a column relying on a different principle than an affinity chromatography column.

5. The process of claim 4, wherein the column volume of the chromatography column of step (ii) is having a column volume of at least 10 L.

6. The process of claim 4, wherein chromatography column of step (ii) is an Ion-exchange chromatography column.

7. The process of claim 1, wherein at least one of the chromatography column(s) in (iii) is a hydroxyapatite column.

8. The process of claim 1, wherein the recombinant cell is an *E. coli* cell.

9. The process of claim 1 wherein the recombinant cell is a nonhuman cell which does not produce an endogenous nonhuman porphobilinogen deaminase.

10. The process of claim 8 wherein the recombinant cell is an *E. coli* cell which does not produce *E. coli* porphobilinogen deaminase.

11. The process of claim 1 in which the rhPBGD is human erythrocyte PBGD.

12. The process of claim 1 in which the rhPBGD is human PBGD encoded by plasmid pExp1-M2-BB, which plasmid is contained in the production strain PBGD-2 deposited as DSM 12915.

13. The process of claim 1 in which the chromatography column of step (ii) is selected from the group consisting of (a) an affinity chromatography column other than a Cibacron Blue 3G affinity chromatography column,
(b) an ion exchange chromatography column,
(c) a hydrophobic interaction chromatography column, and
(d) a hydroxyapatite chromatography column.

14. The process of claim 1 in which the first or only chromatography column of step (iii) is selected from the group consisting of (a) an ion exchange chromatography column,
(b) a hydrophobic interaction chromatography column, and
(c) a hydroxyapatite chromatography column.

15. The process of claim 7 wherein at least one hydroxyapatite column is a ceramic hydroxyapatite column.

* * * * *